United States Patent

Wanunu et al.

(10) Patent No.: US 11,994,508 B2
(45) Date of Patent: May 28, 2024

(54) METHOD AND SYSTEM FOR LINEARIZATION AND TRANSLOCATION OF SINGLE PROTEIN MOLECULES THROUGH NANOPORES

(71) Applicants: Northeastern University, Boston, MA (US); The Board of Trustees of the University of Illinois, Urbana, IL (US)

(72) Inventors: Meni Wanunu, Sharon, MA (US); Luning Yu, Brookline, MA (US); Aleksei Aksimentiev, Urbana, IL (US); Behzad Mehrafrooz, Urbana, IL (US)

(73) Assignees: NORTHEASTERN UNIVERSITY, Boston, MA (US); THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 146 days.

(21) Appl. No.: 17/645,943

(22) Filed: Dec. 23, 2021

(65) Prior Publication Data

US 2022/0283140 A1    Sep. 8, 2022

Related U.S. Application Data

(60) Provisional application No. 63/131,310, filed on Dec. 28, 2020, provisional application No. 63/130,390, filed on Dec. 23, 2020.

(51) Int. Cl.
*G01N 33/487* (2006.01)
*B01L 3/00* (2006.01)
(Continued)

(52) U.S. Cl.
CPC .. *G01N 33/48721* (2013.01); *B01L 3/502715* (2013.01); *B01L 3/502761* (2013.01);
(Continued)

(58) Field of Classification Search
CPC ......... G01N 33/48721; G01N 33/6818; G01N 33/6872; B01L 3/502715; B01L 3/502761;
(Continued)

(56) References Cited

U.S. PATENT DOCUMENTS

2005/0282229 A1* 12/2005 Su ............... G01N 33/48721
                                                                    435/7.1
2014/0318964 A1* 10/2014 Dunbar ......... G01N 33/48721
                                                                    204/601
(Continued)

FOREIGN PATENT DOCUMENTS

WO   WO-2006104311 A1 * 10/2006 ............... B01L 3/50

OTHER PUBLICATIONS

Wilson, James, et al. "Rapid and accurate determination of nanopore ionic current using a steric exclusion model." Acs Sensors 4.3 (2019): 634-644. (Year: 2019).*
(Continued)

*Primary Examiner* — Jennifer Wecker
*Assistant Examiner* — Oyeleye Alexander Alabi
(74) *Attorney, Agent, or Firm* — HAMILTON, BROOK, SMITH & REYNOLDS, P.C.

(57) ABSTRACT

A method and system for performing single molecule proteomics utilizing a nanopore sensor to measure an electronic signature of protein or peptide being transported through the nanopore from a first chamber to a second chamber. The protein's electronic signature is a function of ionic current over time. The method and system utilizing an agent, such as guanidinium chloride, to bind to the nanopore's interior and provide an electroosmotic force within the nanopore. The electroosmotic force, in some embodiments, enables stretching and unfolding of the protein during transport through the nanopore. The agent may also or alternatively
(Continued)

induce the unfolding of the protein before transport through the nanopore and/or provide force moving the protein through the nanopore.

20 Claims, 15 Drawing Sheets
(11 of 15 Drawing Sheet(s) Filed in Color)

(51) Int. Cl.
   *C12Q 1/34* (2006.01)
   *G01N 33/68* (2006.01)
(52) U.S. Cl.
   CPC ........... *C12Q 1/34* (2013.01); *G01N 33/6818* (2013.01); *B01L 2200/0663* (2013.01); *B01L 2300/0645* (2013.01); *B01L 2300/0663* (2013.01); *B01L 2400/0418* (2013.01)
(58) Field of Classification Search
   CPC ..... B01L 2200/0663; B01L 2300/0645; B01L 2300/0663; B01L 2400/0418; C12Q 1/34
   See application file for complete search history.

(56) References Cited

U.S. PATENT DOCUMENTS

| | | | |
|---|---|---|---|
| 2022/0074920 A1* | 3/2022 | Todd | G01N 27/26 |
| 2022/0396758 A1* | 12/2022 | Nivala | G01N 33/54366 |
| 2023/0024319 A1* | 1/2023 | Heron | G01N 33/6818 |
| 2023/0220002 A1* | 7/2023 | Long | C07K 1/128 |
| | | | 530/334 |

OTHER PUBLICATIONS

Benz, et al., "Voltage-Induced Capacitance Relaxation of Lipid Bilayer Membranes—Effects of Membrane Composition," Biochimica et Biophysica Acta, 455 (1976) 721-738.

Bermudez, et al., "Molecular Weight Dependence of Polymersome Membrane Structure, Elasticity, and Stability," Macromolecules 2002, 35, 8203-8208.

Butler, et al., "Single-Molecule DNA Detention with an Engineered MspA Protein Nanopore," PNAS, vol. 105, No. 52, pp. 20647-20652 (Dec. 30, 2008).

Grillo, et al., "Diblock Copolymer Bilayers as Model for Polymersomes: A Coarse Grain Approach," J.Chem. Phys. 146, 244904 (2017).

Japrung, et al., "Urea Facilitates the Translocation of Single-Stranded DNA and RNA Through the α-Hemolysin Nanopore," Biophysical Journal, vol. 98, pp. 1856-1863 (May 2010).

Kang, et al., "One-Pot Species Release and Nanopore Detection in a Voltage-Stable Lipid Bilayer Platform," Nano Lett. 2019, 19, 9145-9153.

Kim, et al., "Comparison of Analytical Methods for Monitoring Autoxidation Profiles of Authentic Lipids," J. Lipid Res., 28: 1110-1117 (1987).

Merstorf, et al., "Wild Type, Mutant Protein Unfolding and Phase Transition Detected by Single-Nanopore Recording," ACS Chem. Biol. 2012, 7, 652-658.

Montal, et al., "Formation of Bimolecular Membranes from Lipid Monolayers and a Study of Their Electrical Properties," Proc. Nat. Acad. Sci. USA, vol. 69, No. 12, pp. 3561-3566 (Dec. 1972).

Onda, et al., "Molecular Recognition of Nucleotides by the Guanidinium Unit at the Surface of Aqueous Micelles and Bilayers. A Comparison of Microscopic and Macroscopic Interfaces,"J. Am. Chem. Soc. 1996, 118, 8524-8530.

Oukhaled, et al., "Unfolding of Proteins and Long Transient Conformations Detected by Single Nanopore Recording," PRL 98, 158101 (2007).

Pantos, et al., "Guanidinium Group: A Versatile Moiety Inducing Transport and Multicompartmentalization in Complementary Membranes," Biochimica et Biophysica Acta 1778 (2008) 811-823.

Pastoriza-Gallego, et al, "Dynamics of Unfolded Protein Transport Through Aerolysin Pore," J. Am. Chem. Soc. 2011, 133, 2923-2931 (Feb. 14, 2011).

Pastoriza-Gallego, et al, "Evidence of Unfolded Protein Translocation through a Protein Nanopore," ACS Nano, vol. 8, No. 11, 11350-11360 (Nov. 7, 2014).

Pastoriza-Gallego, et al, "Urea Denaturation of α-Hemolysin Pore Inserted in Planar Lipid Bilayer Detected by Single Nanopore Recording: Loss of Structural Asymmetry," FEBS Letters 581 (2007) 3371-3376.

Reiter, et al., "Activity of the Gramicidin A Ion Channel in a Lipid Membrane with Switchable Physical Properties," Langmuir 2019, 35, 14959-14966.

Vercoutere, et al., "Rapid Discrimination Among Individual DNA Hairpin Molecules at Single-Nucleotide Resolution Using an Ion Channel," Nature Biotechnology, vol. 19, pp. 248-252 (Mar. 2001).

\* cited by examiner

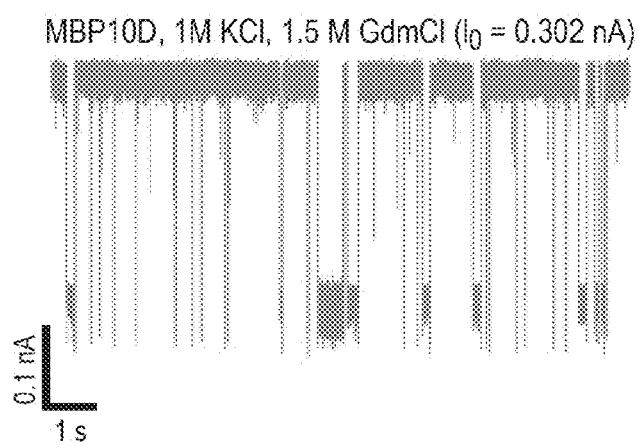 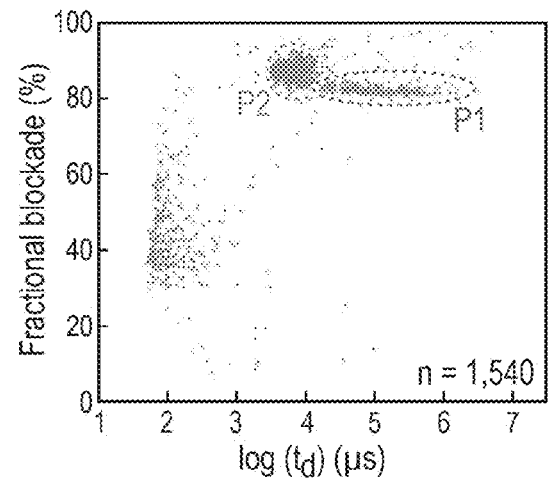
FIG. 2E
FIG. 2F
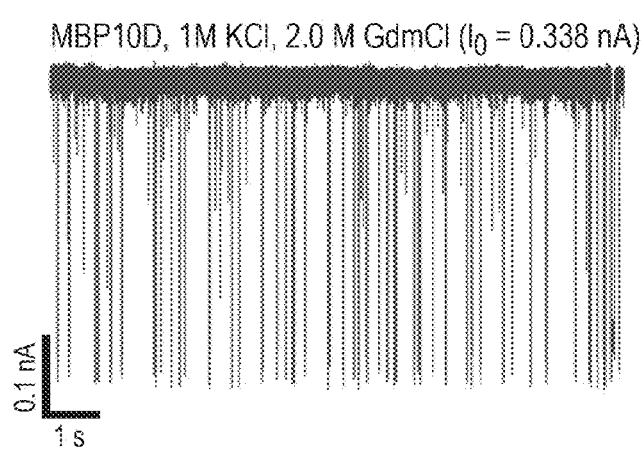 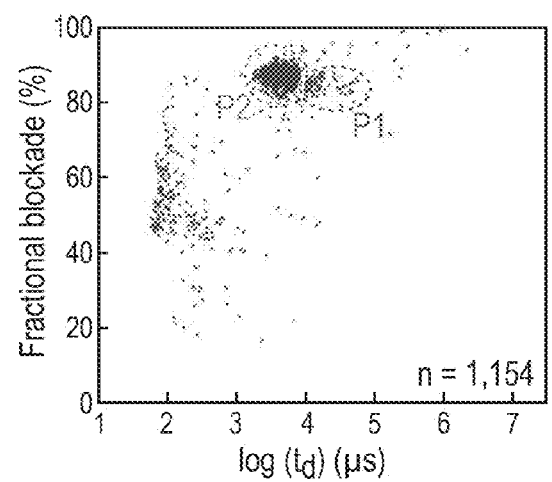
FIG. 2G
FIG. 2H

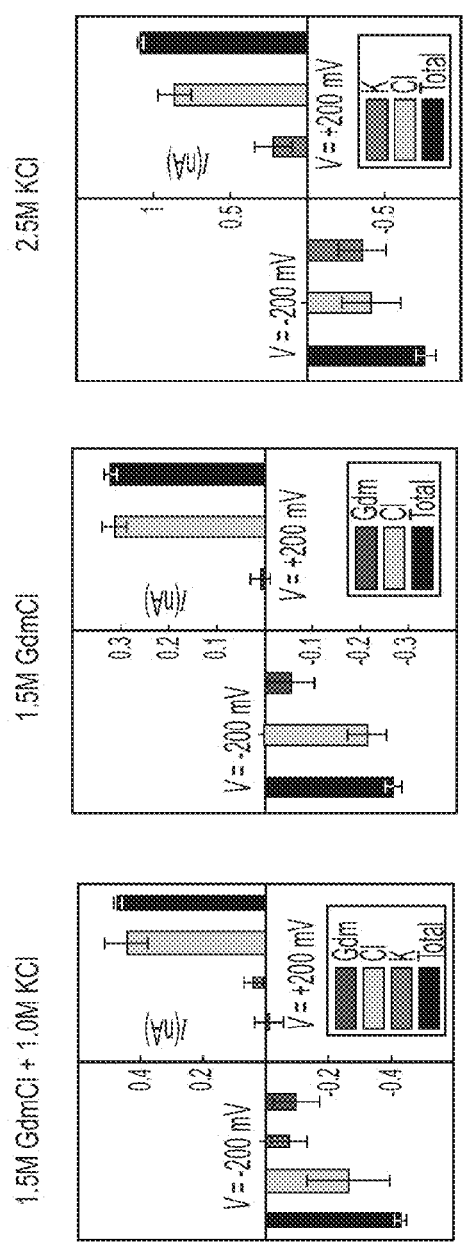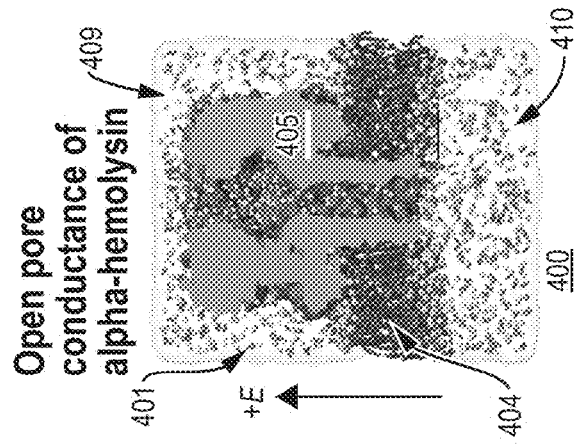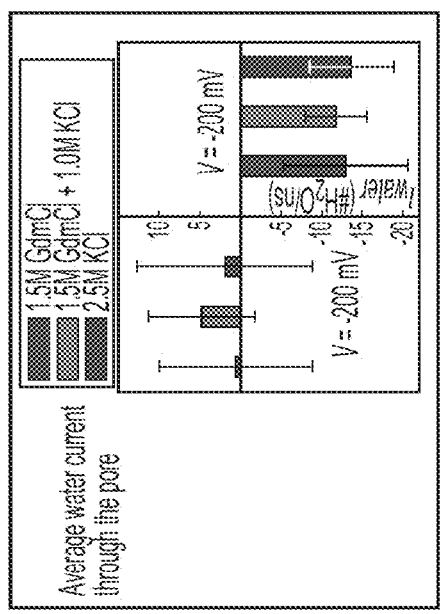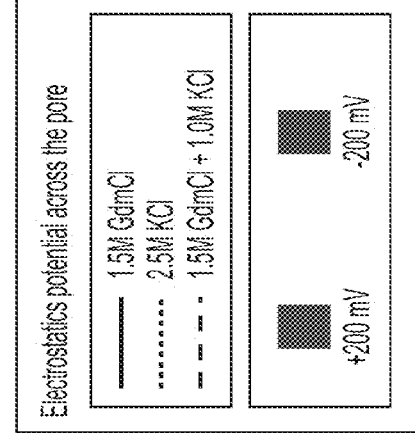
FIG. 4A FIG. 4B FIG. 4C FIG. 4D FIG. 4E FIG. 4F

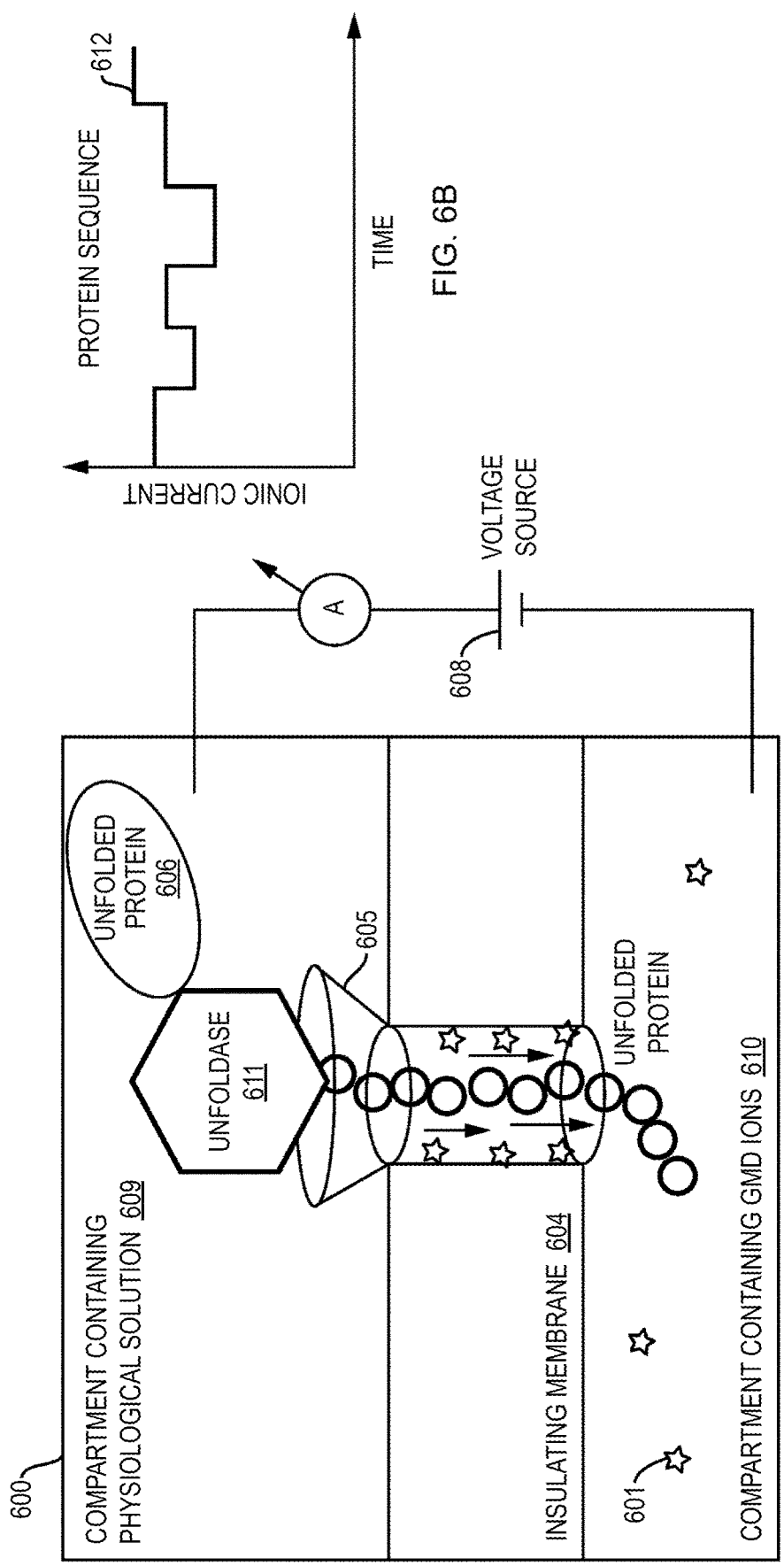

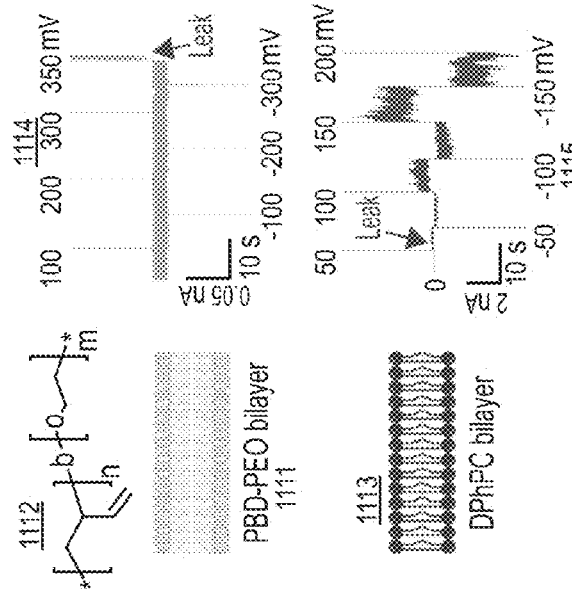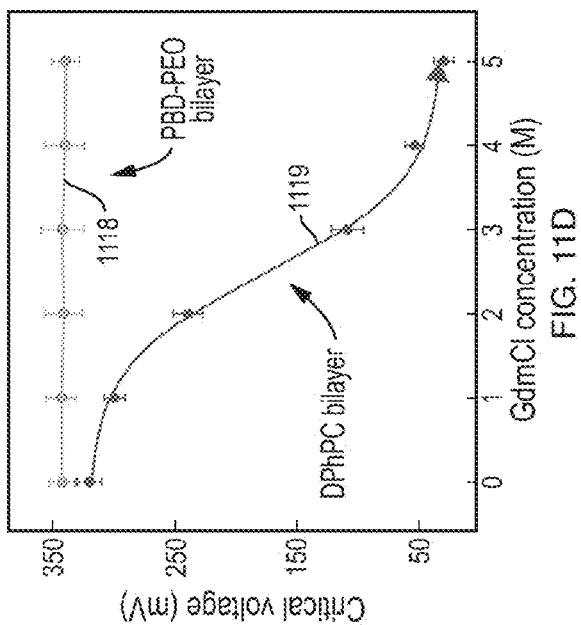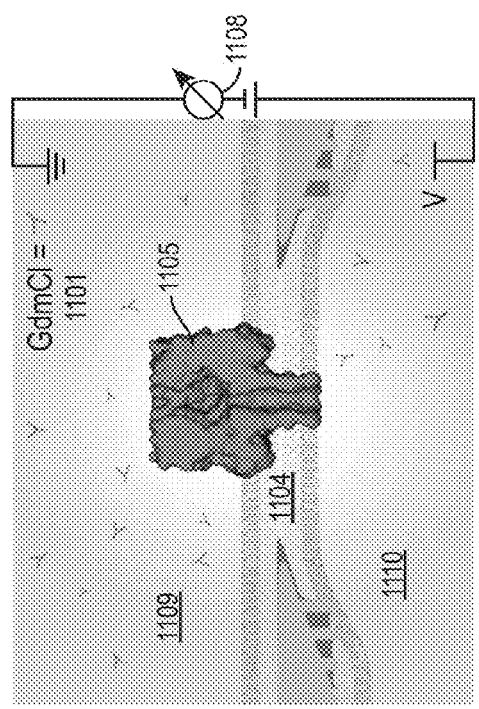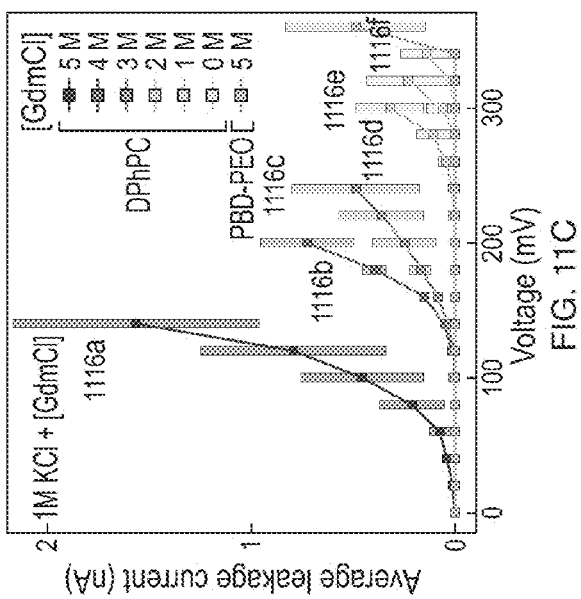

METHOD AND SYSTEM FOR LINEARIZATION AND TRANSLOCATION OF SINGLE PROTEIN MOLECULES THROUGH NANOPORES

RELATED APPLICATIONS

This application claims the benefit of U.S. Provisional Application No. 63/131,310, filed on Dec. 28, 2020, and U.S. Provisional Application No. 63/130,390, filed on Dec. 23, 2020. The entire teachings of the above applications are incorporated herein by reference.

GOVERNMENT SUPPORT

This invention was made with United States government support under R21HG011741 awarded by the National Institutes of Health and under 1827346 awarded by the National Science Foundation. The United States government has certain rights in the invention.

BACKGROUND

Protein identification and/or single-molecule protein sequencing from minute amounts (e.g., single cell levels) could revolutionize the understanding of health by providing a picture of the molecular state of the cell at the level of its most functional molecules. The most used existing tool for protein analysis is a mass spectrometer (MS), which can also detect single biomolecular ions although with enormous difficulty. Indeed, a mass spectrometer can detect the proteome at single cell input levels. However, since proteins are digested/fragmented prior to their detection by a mass spectrometer, and further, since detection efficiency is limited by inefficient ionization of the fragmented peptides, distinguishing different protein isoforms and obtaining a high-fidelity picture of the proteome and its epigenetic state remain outstanding challenges in proteomics. A need exists for a new method of and system for proteome analysis able to analyze a complete full-length protein and able to identify the individual amino acid reside components thereof.

SUMMARY

Adapting nanopore-based nucleic acid sequencing technology to protein sequencing is challenging for several reasons: First, proteins are composed of a chemically more diverse set of building blocks—while DNA and RNA are composed of only 4 nucleotides (excluding modifications), proteins are made up of at least 20 amino acids, and frequently some of these amino acids contain post-translational modifications (PTMs). This necessitates nanopores with resolutions that are superior to the best nanopores used in nucleic acid sequencing (e.g., MspA, CsgG). Second, proteins cannot be chemically cloned or amplified in the same way that DNA and RNA molecules can be replicated using polymerases and/or reverse transcriptases. Therefore, capture of proteins into nanopores must be made highly efficient, especially for applications such as single-cell proteomics. Third, proteins fold into stable and complex tertiary and quaternary structures that are stabilized by multiple types of molecular forces. This higher-order structure complicates the linearization of proteins, a prerequisite to being fed through a nanopore in a regulated manner. Finally, in contrast to the uniformly charged nucleic acids, the peptide backbone of a protein is not charged, with random cationic, anionic, and neutral charge distributions along the peptide. Thus, voltage application across a nanopore does not necessarily generate a force large enough to pull a protein strand taut in the nanopore, as few tens of pN are required to overcome chain entropy (voltage-induced stretching is also seen for a more charged DNA strand). This challenge of stretching the protein is recognized in the community as a critical limitation in the protein readout resolution since the position, or placement, of a specific protein strand within the nanopore is uncontrolled.

A method of performing single molecule proteomics is disclosed herein. The method includes containing a fluid in a structure. The structure defines an interior cavity and a barrier that divides the interior cavity into a first chamber and a second chamber. The barrier contains a channel structure that defines a nanopore therethrough, which fluidically couples the first and second chambers. The nanopore has a flow path bounded by an interior surface of the channel structure. The fluid in the structure includes (i) a protein comprised by amino acid residues therein and (ii) an agent. The agent is capable of binding to the interior surface of the channel structure and further capable of enabling stretching and unfolding of the protein to orient the amino acid residues as a linear series of amino acid residues.

The method further includes applying a voltage gradient between the first chamber and the second chamber via the flow path and still further includes observing an electronic signature of the protein produced by the protein passing through the nanopore. The method also includes determining a property of the protein based on the observed electronic signature.

In some embodiments, the agent may include guanidinium ions. The agent may enable stretching and unfolding of the protein by generating an electroosmotic force in the flow path. The generated electroosmotic force may vary linearly with respect to a magnitude of the voltage gradient. The method may include connecting the protein to a charged tail configured to guide the protein into the flow path when the voltage gradient is applied. The first chamber may contain an enzyme that is capable of causing the protein to unfold. In such embodiments, the agent may not be present in the first chamber.

In one embodiment, the voltage gradient is a first voltage gradient and the method may further include connecting a DNA tail to protein. In such embodiments, the method includes applying a second voltage gradient between the first and the second chambers via the flow path. The second voltage gradient is of sufficient strength to cause a section of the DNA tail to pass through the nanopore prior to the application of the first voltage gradient. In such embodiments, the method also includes activating an enzyme, contained in the first chamber, to draw, in discrete steps, the DNA tail and the connected protein toward the enzyme through the flow path. A DNA structure may be attached to a surface of the nanopore, configured to maintain a separation between the enzyme and the nanopore.

The property of the protein may be at least one of an identity of the protein and an amino acid residue sequence of the protein.

Another example embodiment of the present invention is a system for performing single molecule proteomics. The system includes a structure defining an interior cavity and a barrier dividing the interior cavity into a first chamber and a second chamber. The barrier contains a channel structure that defines a nanopore therethrough, which fluidically couples the first and second chambers. The nanopore has a flow path bounded by an interior surface of the channel structure. The fluid in the structure includes (i) a protein comprised of amino acid residues therein and, (ii) an agent. The agent is capable of binding to the interior surface of the nanopore and further capable of enabling stretching and unfolding of the protein to orient the amino acid residues as a linear series of amino acid residues. The system further includes a voltage source configured to apply a voltage gradient between the first and second chambers via the flow path and still further includes a detector configured to observe an electronic signature of the protein produced by the protein passing through to the nanopore. Finally, the example embodiment of the system includes a processor configured to determine a property of the protein based on the electronic signature.

In some embodiments, the agent may include guanidinium ions. The channel structure of the system may be at least one of a membrane protein and a solid-state nanopore. The protein of the system may be a charged tail configured to guide the protein into the flow path when the voltage gradient is applied. The system may have an enzyme in the first chamber that unfolds the protein. In such embodiments, the enzyme that unfolds the protein is unfoldase.

The protein in the system may be connected to DNA tail. Furthermore, the voltage gradient may be a first voltage gradient and the voltage source may be further configured to apply a second voltage gradient across the first and the second chambers via the flow path. The second voltage gradient is of sufficient strength to cause a section of the DNA tail to pass through the nanopore prior to the application of the first voltage gradient. In such embodiments, the first chamber of the system may also contain an enzyme, capable of drawing, in discrete steps, the DNA tail and the connected protein toward the enzyme through the flow path.

The DNA tail connected to the protein may be comprised of a front portion of single-stranded DNA, a middle portion of double-stranded DNA, and a back portion of single-stranded DNA. In such embodiments, the front portion of single-strand DNA is the section of the DNA tail passed through the nanopore prior to the voltage source applying the first voltage gradient. The system may further include a DNA structure attached to the nanopore, the DNA structure configured to maintain a separation between the enzyme and the nanopore.

The property of the protein may be at least one an identity of the protein and a sequence of the protein.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 2E shows the electronic signals for maltose binding protein with a 10D tail (MBP10D) in a solution of 1 M KCl and 1.5 M GdmCl measured using embodiments of the invention.

FIG. 2F shows the corresponding semi-log scatter plots of fractional blockage percent vs. time for the data in FIG. 2C.

FIG. 2G shows the electronic signals for maltose binding protein with a 10D tail (MBP10D) in a solution of 1 M KCl and 2 M GdmCl measured using embodiments of the invention.

FIG. 2H shows the corresponding semi-log scatter plots of fractional blockage percent vs. time for the data in FIG. 2C.

FIG. 4A shows a molecular dynamics simulation of electro-osmotic flow in an alpha-hemolysin channel structure defining a nanopore.

FIGS. 4B, 4C, and 4D show the result of the simulation in FIG. 4A and the charge carried by the ions across the nanopore under three ionic conditions, (1) a mixture of 1.5 M guanidinium chloride (GdmCl) and 1 M of Potassium chloride (KCl), (2) 1.5 M GdmCl, and, (3) 2.5 M KCl respectively.

FIG. 4E is a graph of the simulated average water current under the different ionic conditions of FIGS. 4B, 4C, and 4D.

FIG. 4F is a graph of the simulated electrostatic potential across the nanopore as a function of channel structure height for +200 mV and −200 Mv for under the different ionic conditions of FIGS. 4B, 4C, and 4D.

FIG. 6A is a diagram of guanidinium ion-assisted protein sequencing, in an example embodiment of the invention.

FIG. 6B is a graph of the function of the ionic current vs. time for the system shown in FIG. 6A.

FIG. 11A a side-view of a bilayer membrane with channel structure defining a nanopore supported by a wedge-on-pillar aperture.

FIG. 11B shows the current vs. time trances for BD-PEO bilayers and DPhPC bilayers when voltage increments are applied in opposite polarities in order to test permeability.

FIG. 11C is a graph of the average leakage current vs. voltage for DPhPC and PBD-PEO bilayer membranes for a range of GdmCl concentrations.

FIG. 11D is a graph of the critical voltage as a function of GdmCl concentration for DPhPC and PBD-PEO membranes.

DETAILED DESCRIPTION

A description of example embodiments follows.

The following disclosure recites a method and corresponding system for full-length protein transport through nanopore sensors. The invention allows for unfolded proteins to be transported across nanopores, one amino acid residue at a time, single-file, and with uniform speeds. Nanopores are innovative sensors that read sub-molecular sections of biopolymers by transmitting ion current while biopolymer strands are electrically passed through the nanopore in a controlled manner. When combining motor enzymes, or other techniques, that are capable of moving biopolymers through the nanopore with high precision and ultra-sharp nanopores of suitable resolution, nanopores can sequence biopolymers such as DNA and RNA with ultra-long read lengths. Typically, DNA and RNA molecules can be passed through nanopores by applying a positive voltage to the collection chamber, because there is an electrophoretic force that pulls the negatively charged nucleic acids through. However, proteins are different because they do not contain a backbone charge, i.e., an amino acid backbone is neutral. In embodiments of the inventions, a combination of an ultrastable polymer membrane and a highly denaturing environment of high guanidinium chloride concentration allows for nanopore measurements of proteins to be taken despite them typically not being achievable under these conditions.

Example embodiments combine the use of a chaotrope (a chemical that changes the hydration shell around a protein molecule for example, guanidinium ions) and an ultra-stable polymer bilayer membrane in order to achieve full-length protein transport through nanopores. One application for this method is single-molecule protein sequencing, and another application is the discovery and quantification of post-translational modifications in proteins. The method and corresponding system provides a highly desired single molecule protein sequencing approach. Embodiments of the invention may be applied to protein sequencing, single-molecule protein sequencing, proteomics, detection of post-translational modifications in single cells, peptide analysis, detection of protein biomarkers and post-translational modifications, and detection of disease biomarkers. In additional the method does not rely on the charge of the protein analyzed so any protein, in principle, can be analyzed. Furthermore, some embodiments of the invention can be performed without the use of enzymes for translocating proteins which is useful because of enzymes' limited lifetime of functionality.

Figure 1:
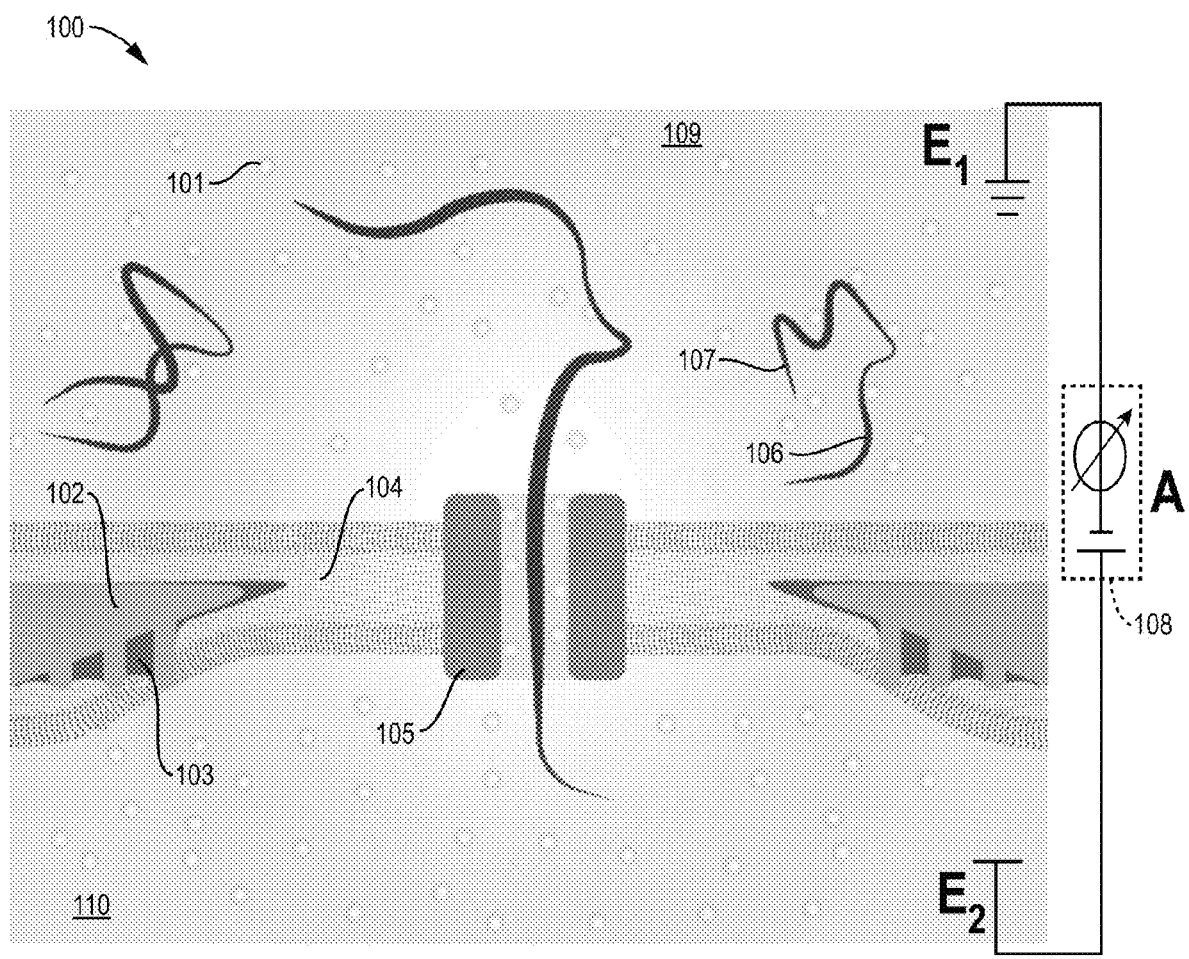
FIG. 1 illustrates a system that allows full-length protein transport through a nanopore sensors, in an example embodiment of the invention.

FIG. 1 illustrates a system 100 that allows full-length protein transport through a nanopore sensor or channel structure 105, in an example embodiment of the invention. System 100 includes a structure with a first chamber 109 and 110. The structure may be a glass or silicon chip that contains a graded SU-8 aperture. The chambers 109 and 110 are capable of containing a fluid, are separated by barrier 104 and are fluidically coupled through nanopore or pore, defined by channel structure, 105 in barrier 104.

Barrier 104 may be an organic polymer membrane layer composed of a synthetic block co-polymer. In such embodiments, the block co-polymer forms an ultrathin film of thickness that can be tuned by adjusting the molecular weight of the polymer, typically around 5 nm. The barrier spans an aperture between supports 102 that is typically 100

µm in diameter, and it serves as an impermeable wall between the cis 109 and trans 110 chambers. In some embodiments, the supports 102 are a solid membrane, such as but not limited to SU-8 polymer, a PTFE aperture, or functional equivalents, that support barrier 104 and can host the planar organic membrane that may form barrier 104 between chambers 109 and 110. In some embodiments, supports 102 may be covered, partially or entirely, in solvent 103 to further support a barrier 104 compose of an organic membrane. The solvent may be decane, hexadecane or any functional equivalent compound.

A pore defined by channel structure 105 through barrier 104 connects chambers 109 and 110. Channel structure 105 may be a trans-membrane nanopore composed of a membrane protein, such as but not limited to, alpha-hemolysin and mutants, MspA and mutants, aerolysin and mutants, CsgG and mutants, and others alike. In one embodiment, the Channel structure 105 is a single-chain MspA provides a unique ability to engineer the pore constriction in an asymmetric way. Engineered octameric MspA was the first protein nanopore to show viability for DNA sequencing. Octameric MspA can be substituted with a single-chain pore by connecting eight MspA subunits using peptide linkers to form single-chain MspA (scMspA). A single-chain protein, such as scMspA enables quick and easy engineering of an asymmetric pore constriction by mutating specific amino acids in only one of the 8 monomeric sequences in the chain and subsequent purification of the protein. Thus, it is possible to design pores based on channel structures 105 using sc7MspA or sc6MspA. In addition, the performance and resolution of the scMspA is comparable to octameric M2-MspA self-assembled from monomers. Finally, both MspA and scMspA 105 defining pores are perfectly stable in the presence of 2M GdmCl, concentrations that denature most proteins in solution. In other embodiments, channel structure 105 may be solid-state nanopore composed of silicon nitride or any other solid material, or a hybrid protein pore embedded in a solid-state pore, such as in a recent paper from the Wanunu group. [Cressiot et al., Nature Communications, Nat Comm, 9, 4652 (2018)]. The pore, defined by channel structure 105, allows fluid, molecules, and ions to move from chamber 109 to chamber 110 despite barrier 104.

The fluid in chamber 109 and/or chamber 110 may include a chaotropic agent 101 (for example, n-butanol, ethanol, guanidinium chloride, lithium perchlorate, lithium acetate, and magnesium chloride) present at high concentrations. The contents of the chambers 109 and 110 may also include some supplemental salt agent (e.g., KCl) and a system for buffering the pH (e.g., tris-HCl). The chaotropic agent binds to the interior surface of channel structure 105 defining the pore and creates an electroosmotic flow in the flow path between chambers 109 and 110. The supplemental salt agent assists ionic flow between the two chambers 109 and 110 through the pore defined by channel structure 105.

Chamber 109 also contains protein molecules 106. The protein molecules 106 are defined by their component amino acid residues. "Amino acid" refers to a molecule containing an amino acid backbone covalently bonded to an amino acid side chain. "Amino acid" includes both naturally-occurring amino acids and non-naturally-occurring amino acids. "Amino acid" also includes canonical amino acids, non-canonical amino acids, L-amino acids and D-amino acids. In one embodiment, an amino acid is a naturally-occurring amino acid.

"Naturally-occurring amino acid" means a compound represented by the formula —N(H)—C(H)(R)—C(O)—, wherein R is the amino acid side chain of a naturally-occurring amino acid (e.g., naturally occurring in proteins, naturally occurring in nature). "Naturally-occurring amino acid" includes both the D- and L-configurations of an amino acid represented by the formula —N(H)—C(H)(R)—C(O)—, wherein R is the amino acid side chain of a naturally-occurring amino acid. When an amino acid is named or depicted by structure without indicating the stereochemistry and has at least one chiral center, it is to be understood that the name or structure encompasses a single enantiomer or diastereomer, a racemic or diastereomeric mixture of the enantiomer or diastereomer(s) and mixtures enriched in one enantiomer or diastereomer relative to its corresponding enantiomer or other diastereomer(s). "Amino acid residue" refers to that portion of an amino acid that is left upon incorporation of the amino acid into a peptide or protein. It will be understood that an amino acid residue is identified herein by reference to the name or structure of its parent amino acid.

The protein molecules are naturally twisted and folded on themselves hindering transport through the pore and preventing accurate analysis. Furthermore, even if the folded proteins move through the pore, their component amino acid residues cannot be isolated and examined individually. Therefore, protein molecules 106 need to be structurally unfolded before being transported through the pore. Protein unfolding may be accomplished in a variety of different manners and with different techniques. In one embodiment, the unfolding is introduced by high concentrations of chaotropic agent 101 in chamber 109. Alternatively, an enzyme located in chamber 109, such as but not limited to unfoldaze, may be used to induce unfolding. In such alternative embodiments, the chaotropic agent 101 may be restricted to chamber 110 and the channel structure 105 interior to prevent it negatively effecting the function of the unfolding enzyme.

Protein molecules 106 may also include a charged tail 107. The charged tail 107 may be attached to the N-terminus or C-terminus of protein molecules 106. The charged tail 107 is configured to orient and guide unfolded protein 106 into channel structure 105 defining the pore when a voltage gradient is applied.

Structure 100 also includes a set of two electrodes E1 and E2, inserted at chamber 109 and chamber 110 respectively. Amplifier 108 can be used to apply voltage to the electrodes E1 and E2 and create a voltage gradient between them. The voltage gradient is applied across chamber 109 and chamber 110 and passes through the interior of channel structure 105 via the pore. The application of the voltage gradient induces an ionic current between chambers 109 and 110 and through the pore. Amplifier 109 may also be used to record the resulting ionic electrical current at fast time intervals. Alternatively, a separate current measurement device and voltage source may be utilized.

When voltage is applied, a circuit is created with electrodes E1 and E2 and amplifier 108. The resistance in the circuit is primarily provided by structure 100 and specifically primarily the pore defined by channel structure 105. If a protein 106 is in the pore, the circuits resistance changes based on the specific protein component amino acid residues in the pore. Therefore, if an unfolded protein is moved through the pore, the resistance of the circuit changes as the protein is transmitted. This change in resistance results in a change in current, measurable by amplifier 109. Both the resistance and the measured amplitude is correlated with the and identity of the protein 106 component amino acid residues and their position relative to the pore. The change in current amplitude over time, during the transport of protein 106 through the pore defined by channel structure 105, is the electronic signature of the transported protein. The electronic signature provides information about the protein's 106 identity or even the sequence of its components amino acid residues.

Structure 100 can be constructed in many ways, in one example embodiment it comprises glass or silicon chip that contains a graded SU-8 aperture, as described in the following work [Kang et al., Nano Letters 19, 9145-9153 (2019)]. The aperture was wetted on both sides using a buffered (Tris HCl, —10 mM, pH 7.5) solution of GdmCl (~1-2M) and KCl (1M). Once wet, a pipette tip can be used to paint an organic film of a block-copolymer solution across the aperture in an organic solvent 103 (decane, hexadecane) in order to form a bilayer membrane 104 that separates between the cis 109 and trans 110 chambers. This membrane 104 prevents ion current from flowing across the aperture. Next a solution that contains a membrane protein (e.g., alpha-hemolysin) is added to the cis chamber 109 and a voltage is applied to monitor the ion current across the membrane 104. When the protein spontaneously incorporates into the membrane 104, it forms a single trans-membrane channel, channel structure 105, indicated by a sudden increase in the ion current. The created channel structure 105 creates a pore that permits the flow of ions between the chamber resulting in a current. Once a single pore is confirmed to be created by the conductance level it produces, protein 106 can be added to chamber 109, where unfolding occurs through incubation with a high concentration of a chaotropic reagent, agent 101, e.g., guanidinium chloride (GdmCl, typically >1M conc.). In one embodiment, GdmCl structurally unfolds protein molecules 106 in chamber 109 by disrupting their secondary structures, provided that there are no contain covalent cross-links between different portions of the protein (e.g., disulfide bridges). GdmCl may also bind to the interior of channel structure 105 to provide further unfolding and stretching force during the transport of protein 106 through the pore. If the protein 106 has a charged tail 107 on one end (e.g., a series of 10 aspartate residues at the C or N termini of the protein), voltage application guides the capture of the protein tail 107, and therefore the attached unfolded protein 106, into the channel structure 105 and the created pore, so that subsequent linearization and threading is facilitated.

When voltage is applied, the ion current signals can be measured and analyzed to learn about the time it takes for unfolded proteins 106 to traverse the pore, and the signal characteristics generated during each protein component amino acid residue's passage. As the protein transmits through the pore, its component amino acid residues block the transit of ions increasing the resistance of structure 100 and reducing the ion current. The signal characteristics depend on and can be used to provide information regarding the protein's 106 identity and sequence.

Figures 2A, 2B:
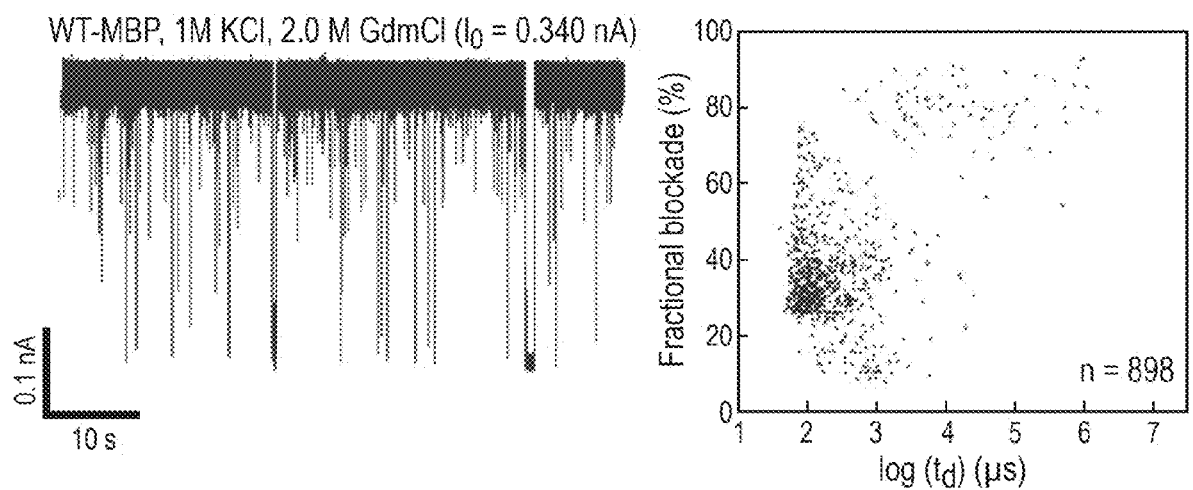
FIG. 2A shows the electronic signals for wild type maltose binding protein (WT-MBP) in a solution of 1 M KCl and 2 M GdmCl measured using embodiments of the invention.
FIG. 2B shows the corresponding semi-log scatter plots of fractional blockage percent vs. time for the data in FIG. 2A.
Figures 2C, 2D:
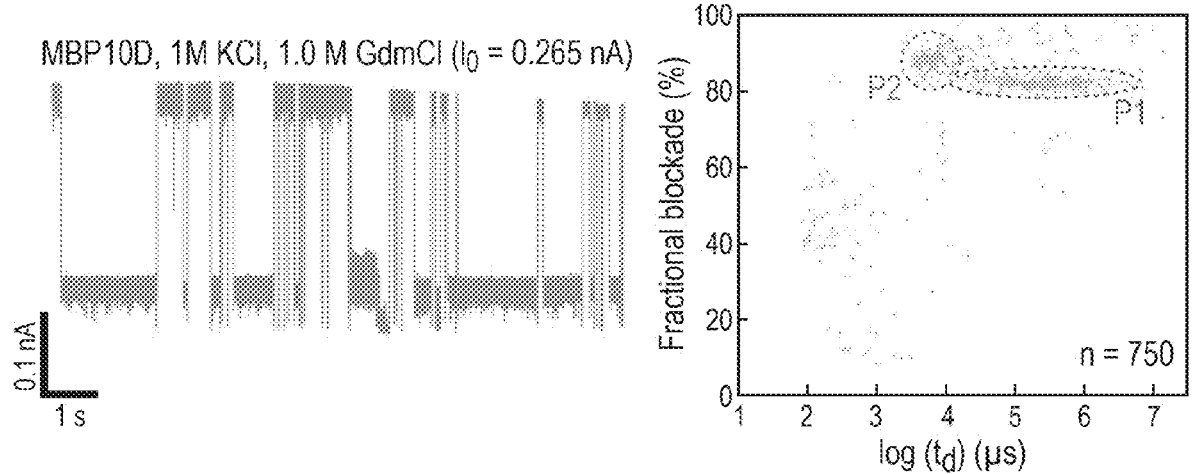
FIG. 2C shows the electronic signals for maltose binding protein with a 10D tail (MBP10D) in a solution of 1 M KCl and 1 M GdmCl measured using embodiments of the invention.
FIG. 2D shows the corresponding semi-log scatter plots of fractional blockage percent vs. time for the data in FIG. 2C.

FIGS. 2A, 2C, 2E, and 2G show the electronic signals for maltose binding protein (MBP) under different conditions measured using embodiments of the invention. The graphs in FIGS. 2A, 2C, 2E, and 2G show the measured current (y-axis) vs. time (x-axis) as the maltose binding protein is being transposed through the pore. The graphs in FIGS. 2A, 2C, 2E, and 2G are labeled with the protein used, ion (GdmCl) and salt concentration (KCl) in structure 100 and initial current applied by amplifier 108. The reduction in ionic current as proteins move through the pore can be clearly seen in all of the graphs in FIGS. 2A, 2C, 2E, and 2G. Scatter plots in in FIGS. 2B, 2D, 2F, and 2H correspond to the graphs in FIGS. 2A, 2C, 2E, and 2G and show the of the fractional current blockade vs. the dwell times of the blockade events (in log scale) caused by the protein 106 in the pore defined by channel structure 105. FIG. 2A and FIG. 2B show the results of a wild-type maltose binding protein (WT-MBP) while graphs FIGS. 2C, 2E, and 2G and corresponding FIGS. 2D, 2F, and 2H show the results of a MBP with a c-terminus D10 tail 107 (MBP10D). For all FIGS. 2A, 2C, 2E, and 2G the displayed data was captured by transmitted the aforementioned proteins through a a-hemolysin channel structure 105 defining a pore with a voltage of 175 mV. In FIGS. 2B, 2D, 2F, and 2H, labeled population P1 is the data for the transport of partially unfolded proteins, and labeled population P2 is the data for the transport of fully unfolded proteins. As shown in FIG. 2A, for wild-type MBP, most of the events are short-lived with very small fractional blockade percentage resulting in an unclear electronic signature, whereas, as shown in FIGS. 2C, 2E, and 2G, for the MBP that has a D10 tail, longer and more complete blockade events are observed. FIGS. 2B, 2D, 2F, and 2H also show that that two populations dominate, P1 and P2, corresponding to partly unfolded and fully unfolded protein, respectively. At 2M GdmCl, almost all of the protein is unfolded, indicated by a dominant P2 population in FIG. 2H. As a result, the electronic signature shown in FIG. 2G is clearly defined with individual protein amino acid residue's effect on the measured current visible.

Figure 3A:
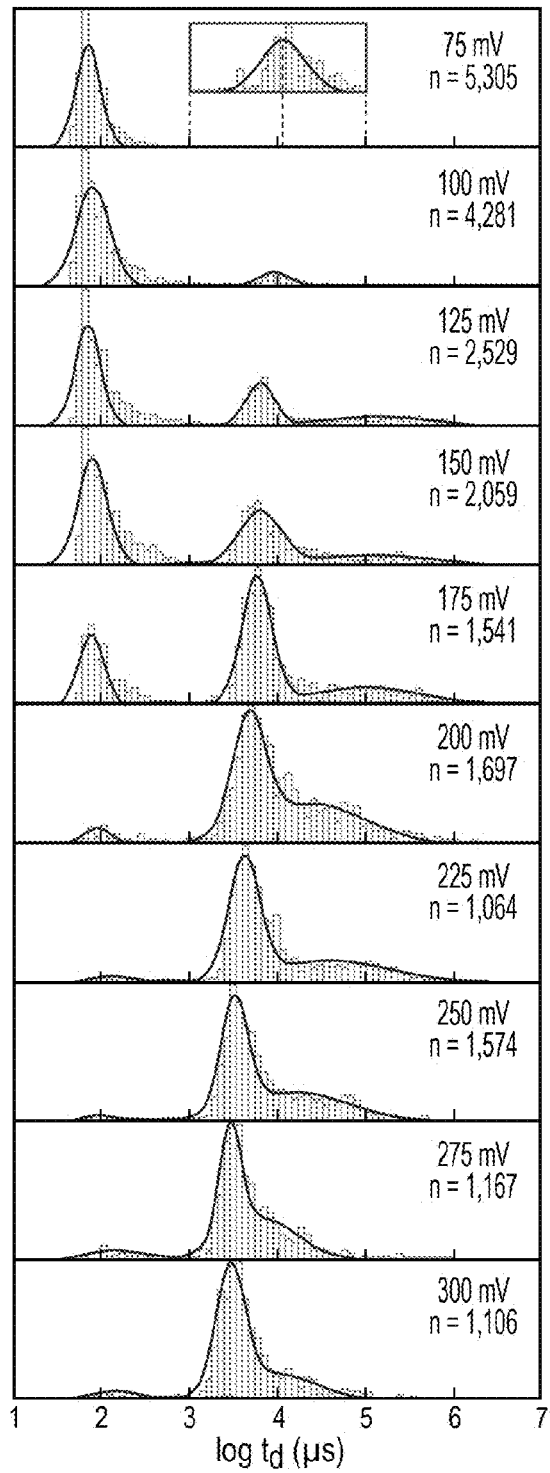
FIG. 3A shows the histograms of dwell time in a a-hemolysin channel structure defining a nanopore and corresponding semi-log plots of maltose binding protein with a c-terminus D10 tail (MBP10D), at different voltages in embodiments of the invention.
Figure 3B:
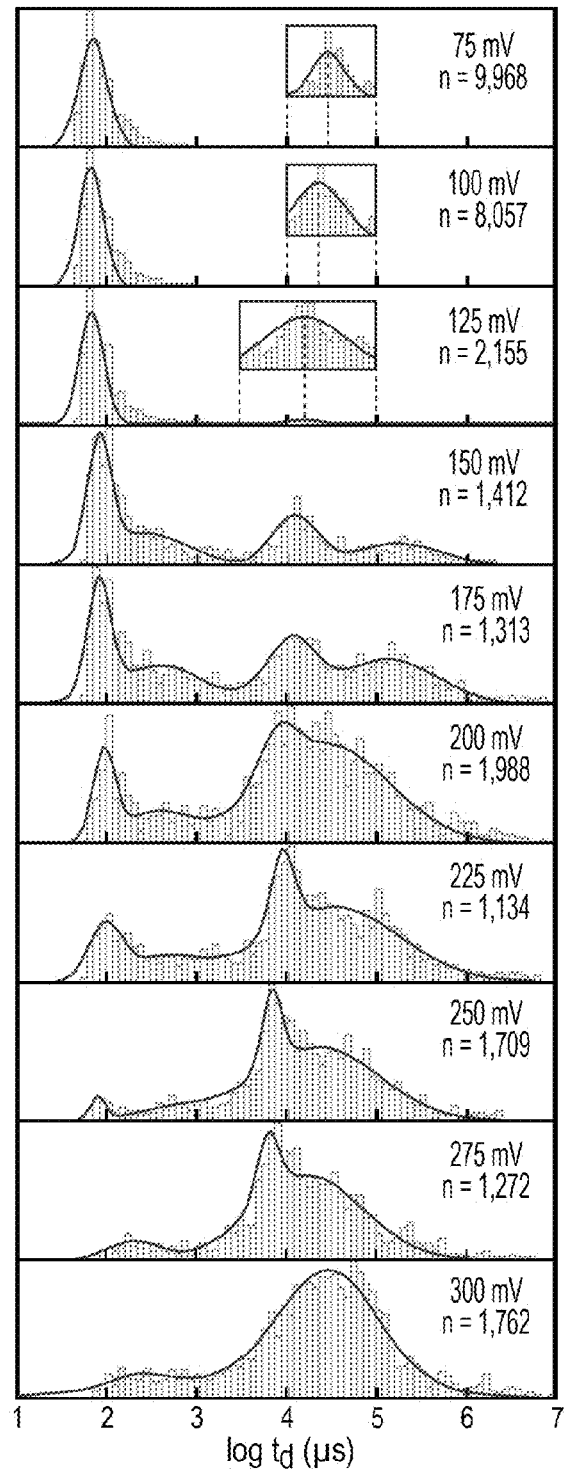
FIG. 3B shows the histograms of dwell time in a a-hemolysin channel structure defining a nanopore and corresponding semi-log plots of a concatemer of maltose binding protein and maltose binding protein with a c-terminus D10 tail (MBPMBP10D).
Figure 3C:
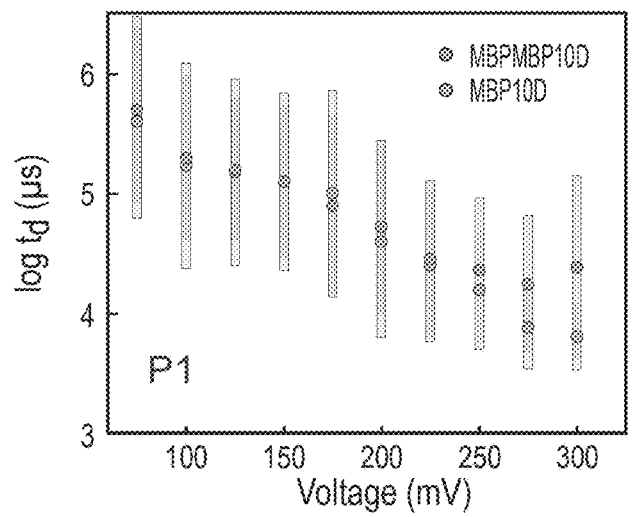
FIG. 3C and FIG. 3D are semi-log plots that show the protein dwell time as a function of voltage for population P1, folded protein population P2, and unfolded protein respectively for the same data shown in FIGS. 3A and 3B.
Figure 3D:
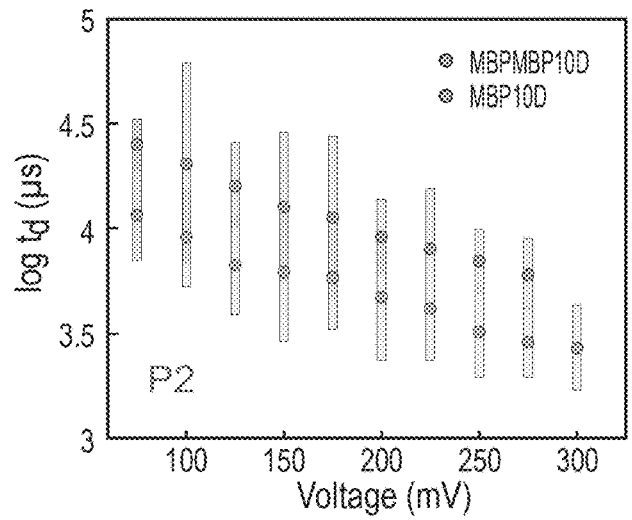
Figure 3E:
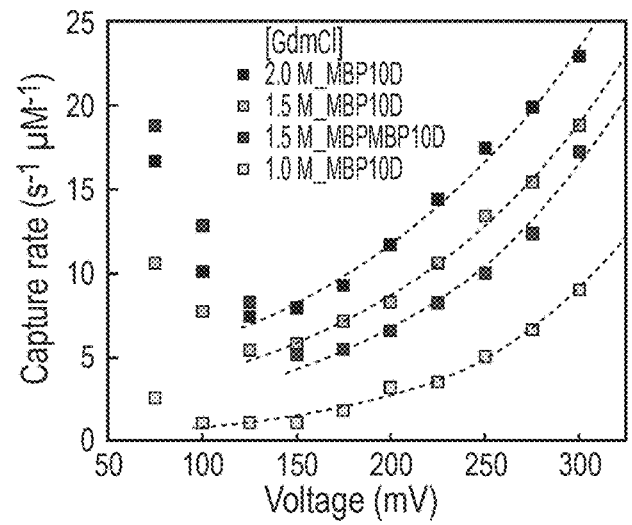
FIG. 3E is a semi-log plot that shows concentration-normalized capture rates for proteins (MBP10D and MBPMBP10D) under different conditions, such as concentration of agent (1.0 M to 2.0 M of GdmCl), as a function of voltage.

FIG. 3A shows the histograms of dwell time in a a-hemolysin channel structure 105 defining a pore and corresponding semi-log plots of maltose binding protein with a c-terminus D10 tail 107 (MBP10D, at different voltages in embodiments of the invention. FIG. 3B shows the histograms of dwell time in a a-hemolysin 105 defined pore and corresponding semi-log plots of a concatemer of maltose binding protein and maltose binding protein with a c-terminus D10 tail 107 (MBPMBP10D), at different voltages in embodiments of the invention. Histograms in FIG. 3A show the dwell time in a a-hemolysin 105 defined pore of monomeric MBP10D obtained in 1.5M GdmCl/1MKCl electrolyte at different voltages from 75 mV to 300 mV. Histograms in FIG. 3B show the dwell time a a-hemolysin 105 defined pore of a concatemer of maltose binding protein and MBP with a c-terminus D10 tail 107, MBPMBP10D, at different voltages from 75 mV to 300 mV. Histograms in FIGS. 3A and 3B illustrate that the translocation times of protein 106 through the pore, or event dwell times (td), get shorter with increasing voltage, which is the clear mark of a translocation process (i.e., all of the protein residues traverse the pore from chamber 109 to chamber 110). In addition, FIG. 3E shows that the protein capture rates increase with increasing GdmCl, used as agent 101, concentrations in the electrolyte. This implies that increasing the GdmCl concentration, or other similar agents 101, results in a stronger driving force for the proteins to enter and traverse the pore, as well as to be pulled and stretched within the pore. Semi-log plot in FIG. 3C shows protein dwell time as a function of voltage for population P1, folded proteins 106 for the same data shown in histograms 301 and 302. Semi-log plot in FIG. 3D shows the protein dwell time as a function of voltage for population P2, unfolded protein 106 for the same data shown in FIGS. 3A and 3B. In P2, the unfolded protein, the difference between the two proteins, MBP10D and MBPMBP10D, is more clearly expressed. Semi-log plot in FIG. 3E shows concentration-normalized capture rates for proteins (MBP10D and MBPMBP10D) 106 under different conditions, such as concentration of agent 101 (1.0 M to 2.0 M of GdmCl), as a function of voltage. For the proteins tested, an increase and voltage and agent 101 concentration is correlated with improved capture rate of protein 106 with tail 107 in the pore defined by channel structure 105. These results, illustrate that both the unfolding, accomplished by agent 101, and the attached tail 107 interacting with the applied voltage assist in the threading and transporting of protein 106 into and through the pore.

In the presence of GdmCl, smooth translocation of full-length proteins, from 254-764 amino acids were observed (smooth refers to the velocity of the proteins being more or less constant). Even though the proteins 106 contained regions of negative and positive charges along the backbone, the mean protein velocities observed were slow and uniform, about 10 μs/aa (~30%) in 2 M GdmCl strength at 175 mV. This translocation rate is over 1 order of magnitude slower than the for case of DNA translocation through the same pore at a similar voltage.

FIG. 4A shows a molecular dynamics simulation of electro-osmotic flow in an alpha-hemolysin defined nanopore or pore. Simulation 400 shows a typical molecular dynamics system including a membrane 404 separating chamber 409 and 410 containing a single alpha-hemolysin structure channel 405 insulated in the membrane 404 defining a pore through the membrane 404. Simulation 400 models the behavior of a mixture of water, an agent 401, in this case guanidinium chloride, and an electrolyte, in this case KCl, in that system when a voltage, +E, is applied.

FIGS. 4B and 4D show the result of the simulation 400 in FIG. 4A and the charge carried by the ions across the nanopore under three ionic conditions, (1) a mixture of 1.5 M guanidinium chloride 401 (GdmCl) and 1 M of Potassium chloride (KCl), (2) 1.5 M GdmCl 401, and, (3) 2.5 M KCl respectively. For each ionic condition, FIGS. 4B to 4D show the result of the simulation 400 for a −200 mV and +200 mV applied voltage. The magnitude and make-up of the simulated ionic current through the nanopore was found to depend on the polarity of the transmembrane bias, with the biggest difference being the relative contribution of cationic and anionic species. FIG. 4E is a graph of the simulated average water current under the different ionic conditions and a −200 mV and +200 mV applied voltage. Under a positive bias, the current was found to be carried predominantly but the guanidinium chloride ions, which produced a substantial electro-osmotic flow. FIG. 4F is a graph of the simulated electrostatic potential across the nanopore as a function of channel structure height for +200 mV and −200 mV for under the different ionic conditions. The type and concentration of the electrolyte, e.g. KCl, was found to have a rather minor effect on the distribution of the electrostatic potential in the nanopore.

Figure 5A:
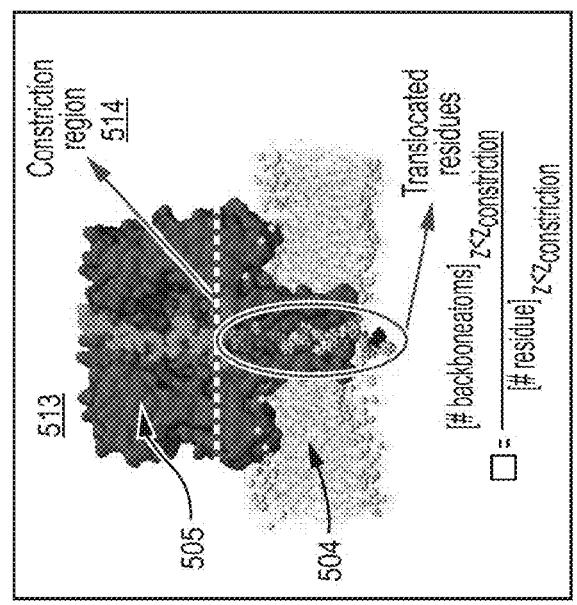
FIG. 5A is a molecular dynamics simulation of peptide translocation through an alpha-hemolysin channel structure defining a nanopore in mixture of 1.5M GmdCl and 1 M KCl.

FIG. 5A is a molecular dynamics simulation 500 of peptide translocation through an alpha-hemolysin 505 defined pore in a mixture of 1.5M GmdCl and 1 M KCl. Simulation 500 shows a typical molecular dynamics system including a membrane 504 separating chamber 509 and 510 with a single alpha-hemolysin channel structure 505 insulated in the membrane 504 defining a pore through the membrane 504. Simulation 500 models the behavior of a mixture of water, an agent 501, in this case guanidinium chloride, an electrolyte, in this case KCl, and peptide 506 in that system when a voltage, +E, is applied. In simulation 500, peptide 506 is a fragment of unfolded protein threaded through an alpha-hemolysin 505 defined nanopore. Seven simulation systems were constructed, each featuring different parts of the MBD protein. The system 500 was simulated under a +200 mV transmembrane bias or voltage gradient, the resulting flux of ions, water and atoms comprising peptide 506 were recorded.

Figure 5B:
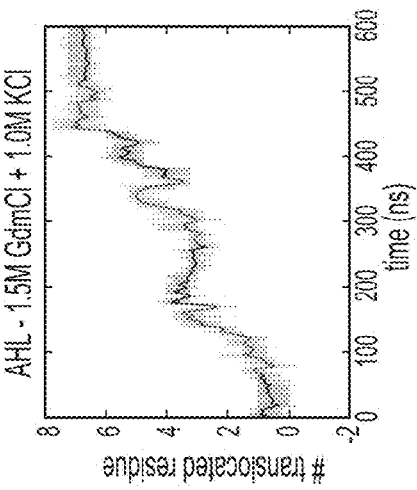
FIG. 5B is a graph of the function of cumulative current through a nanopore as a function of time for the simulation shown in FIG. 5A.

FIG. 5B is a graph of the function of cumulative current through the pore as a function of time for simulation 500 shown in FIG. 5A. The resulting simulation data in FIG. 5B shows that the ionic current through alpha-hemolysin 505 defined pore was blocked by the peptide 506 and this blockage is facilitated by the displacement of chloride ions by the peptide 506, whereas the current from guanidinium ions 501 is negligible.

Figure 5C:
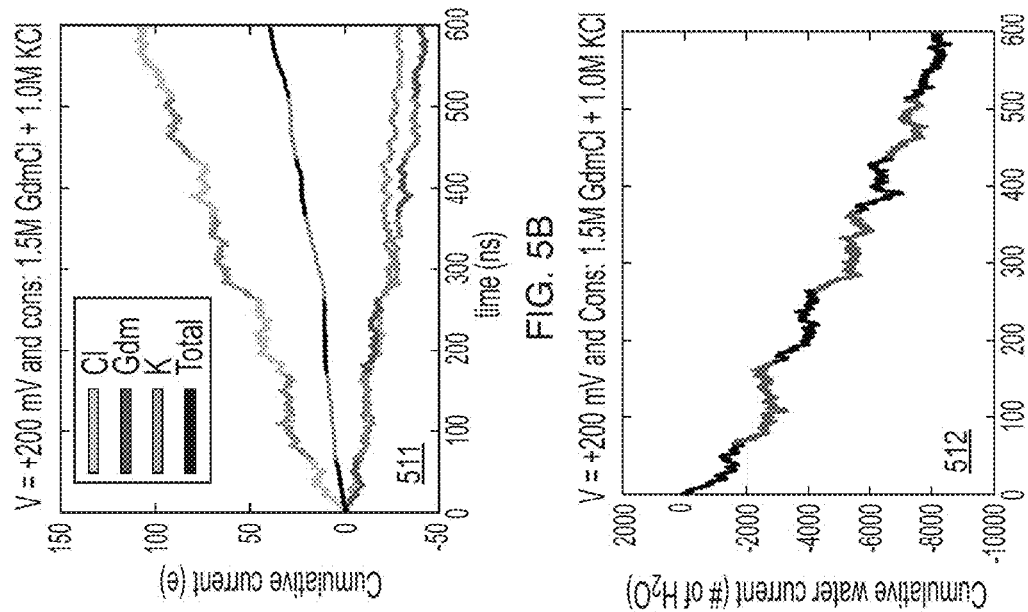
FIG. 5C is a graph of the cumulative water current through a nanopore as a function of time for the simulation shown in FIG. 5A.

FIG. 5C is a graph of the cumulative water current through the nanopore as a function of time for simulation 500 shown in FIG. 5A. The resulting simulation data in FIG. 5C shows the cumulative water current as a function of time. The high flux of chloride ions was found to generate a steady flow of water directed downward through the nanopore.

Figure 5D:
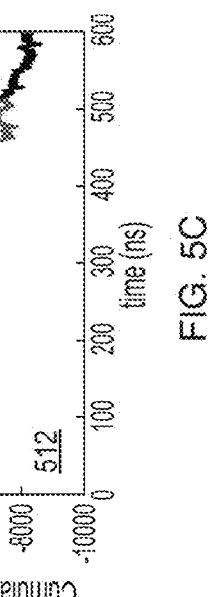
FIG. 5D is a simulation of a nanopore transporting a protein through a barrier with an identified constriction region.

FIG. 5D is a simulation 513 of a the pore transporting a protein 506 through a barrier membrane 504 with an identified constriction region 514 of channel structure 505. Simulation 513 identifies the location of the constriction 514 relative to channel structure 505 and membrane 504. To quantify the displacement of peptide 506 through the nanopore, the number of peptide residues that passed through the alpha-hemolysin 505 constriction 514 were counted. That number was determined by dividing by the number of peptide 506 backbone atoms passed constriction 514 by the total number of atoms in a peptide 506 backbone.

Figure 5E:
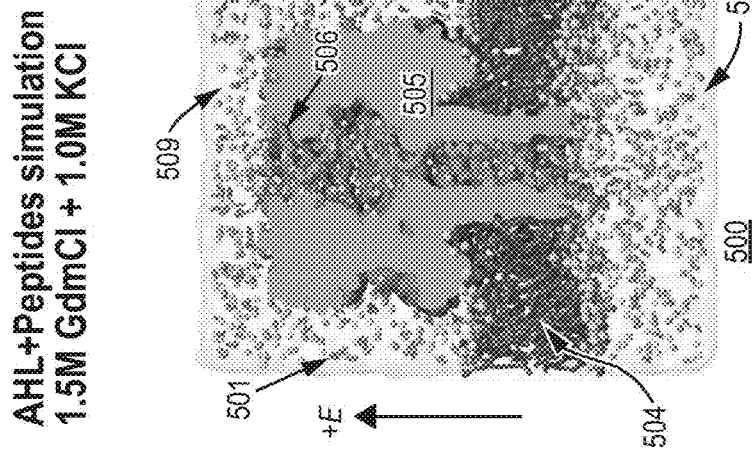
FIG. 5E displays the results of a calculation of the displacement of peptide through a nanopore as a function of time for the simulation shown in FIG. 5A.

FIG. 5E displays the results of a calculation of the displacement of peptide 506 through the nanopore as a function of time for simulation 500 shown in FIG. 5A. Simulation 500 shows that the electro-osmotic flow through the nanopore pushes the peptide 506 down through nanopore at a rate of several residues per microsecond. Therefore, the electroosmotic flow generated by ions of agent 101, e.g. the GdmCl 501 on the walls of channel structure 505 defining the nanopore, is a dominant mechanism in the transport of proteins 106 or peptides 506 through the a-hemolysin 505 defined nanopore, 104. In other words. due to large residence times of Gdm$^+$501 ions on the channel structure 505 walls, which renders the pore positively charged and promotes Cl$^-$ electroosmosis that pulls the protein backbone through the pore.

FIG. 6A is a diagram of guanidinium ion (Gdm+) assisted protein sequencing, in an example embodiment of the invention. A structure has two chambers 609 and 610 separated by an insulating membrane 604 and fluidically coupled by a pore, defined by channel structure 605, through membrane 604. Protein 606 is located in chamber 609 with enzyme 611, which may be unfoldase or another protein-translocation enzyme. Agent 601, which in such embodiments including the one shown in FIG. 6A may be guanidinium ions, is located in chamber 610. In the embodiment shown in FIG. 6A, the agent 601 is kept out of chamber 609 to avoid negative interactions with enzyme 611. This may be accomplished using the asymmetric buffer composition and the strong electro-osmotic effect. Agent 601 is still bound to the interior of channel structure 605 defining the pore and provides the electroosmotic flow force for transport of protein 606. Agent 601 may be bound to the interior of channel structure 605 defining the pore by diffusion and/or convection from the trans chamber 610 of the membrane 604. Voltage source 608 provides a voltage gradient between chambers 609 and 610 resulting in an ionic current passing through the pore. Voltage source 608 may also measure the ionic current as a function of time. Alternatively, a separate ammeter may measure the ionic current.

Protein 606 is unfolded and threaded into the pore by enzyme 611. In this embodiment 600, tail 607 is not required as enzyme 611 accomplishes a similar function. Once protein 606 is inside the pore, the guanidinium ions 601 on the interior of channel structure 605 defining pore provide an unfolding and stretching force that keeps protein 605 unfolded and transports it through the pore to chamber 610. Binding of guanidinium ions 601 to the interior of the channel structure 605 surface defining the pore or nanopore produces a strong electro-osmotic effect that pushes the unfolded peptide 606 chain down through the nanopore, ensuring unidirectional transport. As protein 605 moves through pore, its component amino acid residues alter the resistance of the pore. For example, in some embodiments, by displacing or blocking salt ions, such as chloride that provide the majority of the ionic current as show in the results of simulation 400. Different protein 606 component amino acid residues change the resistance by different amounts. This varying resistance provides a measurable function of ionic current over time. This function is the electronic signature of protein 606 and can be used to identify and analyze the protein 606.

FIG. 6B is a graph of the function of the ionic current vs. time for the system shown in FIG. 6A. The identity and/or sequence of the protein 606 may be recorded by analyzing the electronic signature 612 of the protein that is based on the modulation of the ionic current flowing through the nanopore.

Figure 7:
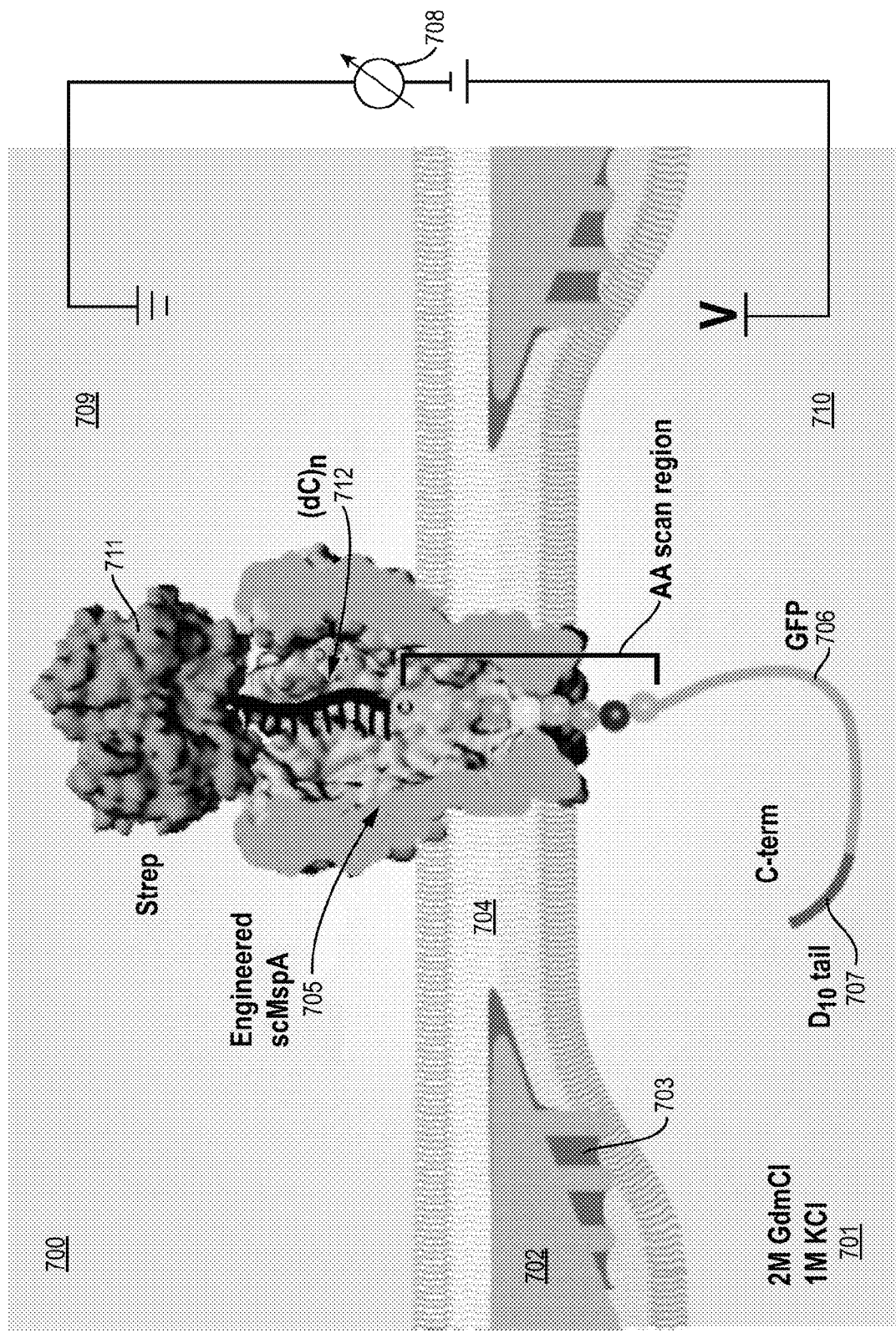
FIG. 7 illustrates a system that allows protein sequencing using nanopore sensors, in an example embodiment of the invention.

FIG. 7 illustrates a system 700 that allows for protein sequencing using nanopore sensors, in an example embodiment of the invention. Structure 700 has two chambers 709 and 710 separated by a membrane 704 supported by supports 702 covered in solvent 703. Channel structure 705 defines a pore or nanopore that provides a flow channel through membrane 704 and connects chambers 709 and 710. Channel structure 704 may be a scMspA pore.

Protein 706 is located in chamber 710 and may be modified with a charged tail 707 and a poly(dC)n oligonucleotide 712. Protein 706 may be a green-fluorescent protein (GFP) already unfolded based on interactions guanidinium ions. Enzyme 711 is located in chamber 709 and may be a streptavidin anchor. Enzyme 711 links to the $(dC)_n$ molecules 712 attached to protein 706 and is used to immobilize a component amino acid sequence of protein 706. Enzyme 711 may be configured to pull the $(dC)_n$ molecules 712, towards chamber 709. This also results in an applied force on the attached protein 706. Agent 701, for example GdmCl, is present in chamber 710. In one example embodiment, chamber 710 has a buffer condition of 2M GdmCl+1M KCl. The guanidinium ions will bind to the interior surface of channel 706 and induce an electroosmotic flow in pore and be used to pull and stretch protein 706 in pore 705 keeping it linear and unfolded. This accomplishes the critical challenge of pulling the protein 706 taut in pore 705 during the protein readout process.

Amplifier 708 is used to apply a voltage gradient between chambers 709 and 710 and induce the flow of ionic current through the pore. As enzyme 711 pulls the $(dC)_n$ molecules 712 towards chamber 709, the guanidinium ions in on the surface of channel structure 705 that defines the pore will apply a force towards chamber 710. These opposing forces keep the amino acid scan region of protein 705 within the pore unfolded and taut. Therefore, by measuring the ionic current, the amino acid scan region of protein 705 within the pore can be analyzed.

Figure 8A:
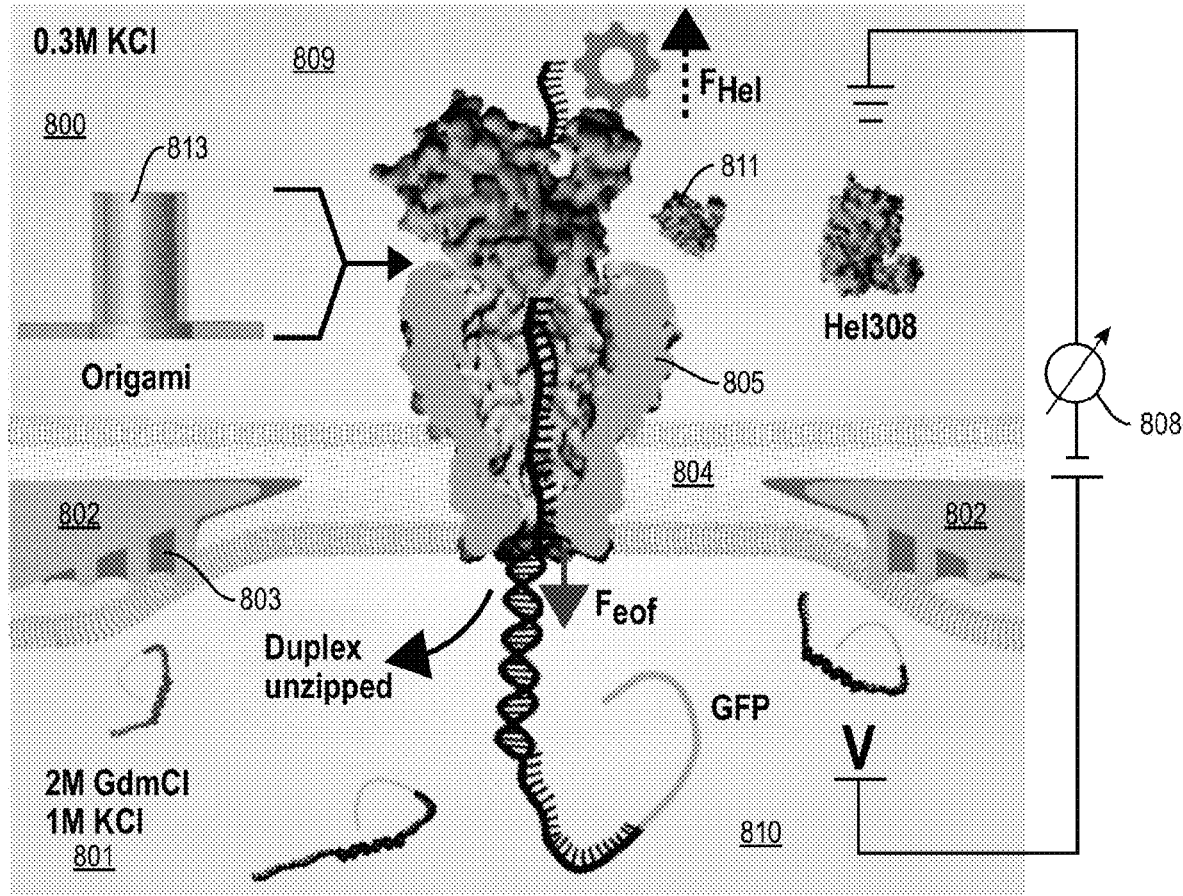
FIG. 8A illustrates a system that allows full length protein sequencing using nanopore sensors, in an example embodiment of the invention.

FIG. 8A illustrates a system 800 that allows full-length protein sequencing using a nanopore sensors, in an example embodiment of the invention. Structure 800 has two chambers 809 and 810 separated by a membrane 804 supported by supports 802 covered in solvent 803. Channel structure 805 defines a pore and provides a flow channel through membrane 804 and connects chambers 809 and 810. Channel structure 804 may be a scMspA pore.

Figure 8B:
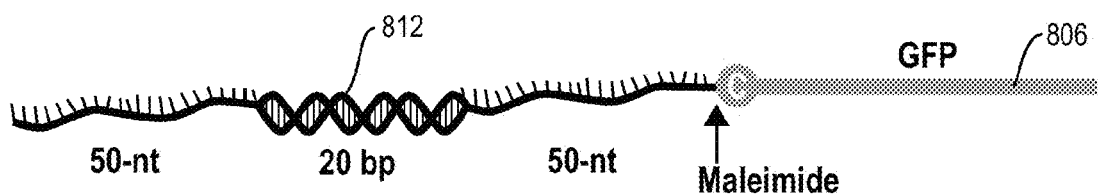
FIG. 8B is a depiction of a protein with an attached DNA strand.

Protein 806 is located in chamber 810. Protein 806 may be a green-fluorescent protein (GFP). Protein 806 may be attached to DNA strand or tail 812. In alternative embodiments protein 806 may be attached to a RNA strand or tail. FIG. 8B is a depiction of a protein with an attached DNA strand. The DNA strand 812 may be a 120-mer with a 50-mer single stand section connected to a 20-mer duplex section that is then connected to a second 50-mer single strand section. The DNA strand 812 may be attached to the N-terminal cysteine of a subset of the GFP protein 806. The may alternatively be attached to the C-terminus of the GFP protein 806. The 120-mer DNA strand 812 may be prepared by a splint ligation (T4 ligase) of a 60-mer DNA oligo containing a 5' thiol modifier to a 60-mer DNA oligo in the presence of a 20-mer splint that has overlapping sequences complementary to the 60-mers.

Chamber 810 has a mixture of an electrolyte, in this non-limiting example 1.0 M of KCl and an agent 801, in in this non-limiting example 2.0 M of GdmCl. The agent 801 may be used to unfold protein 806 in chamber 810. Chamber 809 contains only the electrolyte, in this non-limiting example 0.3 M of KCl. Chamber 809 also contains a helicase-mediated protein translocation platform 811 that may be an enzyme for non-limiting example Hel308. Ammeter 808 acts as a voltage source and a measurer of the resulting ionic current.

Structure 800 allows for the full-length sequencing of protein 806. In step one, a negative voltage gradient is applied that has sufficient strength to thread into and pass a section of DNA strand 812 through a pore or nanopore defined by channel structure 805 from chamber 810 to chamber 809. If DNA strand 812 has a duplex section, the duplex section will act as a stop gap and prevent the transportation of the entire DNA strand and attached protein 806. In step 2, an enzyme such as Hel308 811, in chamber 809, binds to the end of the DNA strand 812. This binding may take approximately 10-50 ms. After the binding is complete, the voltage is reversed. This new positive voltage results in the ions of agent 801, inducing an electroosmotic flow force ($F_{eof}$) within the pore and towards chamber 810. However, in step 3, Hel308 811 will provide a counter force $F_{hel}$ towards chamber 809 as it ratchets along the DNA strand 812 in discrete steps. Hel308 unzips the duplex section of DNA strand 812 and ratchets up to 20 GFP 806 amino acids towards the enzyme and through the pore. $F_{hel}$ moves the DNA strand 812, and attached protein 806, through the pore while $F_{eof}$ provides the necessary unfolding and stretching force within the pore. These dual forces should move the protein 806 through the pore in a sufficiently slow and controlled manner to measure the protein's electronic signature based on change in the ionic current. This electronic signature can then be used to sequence protein 806.

However, since Hel308 811 can only bind to DNA, once it has moved through the entirety of DNA strand 812, it can no longer apply $F_{hel}$ and the protein 806 stops moving through the pore. This can occur before the entirety of protein 806 is translocated. However, a solution exists in the addition of spacer 813 to structure 800. Spacer 813 creates a distance between the pore and Hel308 811, or equivalent source of upward force on protein 806. By adding this additional space, it ensures that more of protein 806 is translocated through the pore before Hel308 811 runs out of DNA strand 812. Therefore, Spacer 813, can be used to increase protein 806 read lengths. Spacer 813 may be a DNA origami structure, and in one non-limiting example, a 30 nm long DNA origami barrel. In embodiments that utilize spacer 813, DNA stand 812 may be extended in order to ensure it extends outside spacer 813 and binds with Hel308 811 or an equivalent enzyme.

Figure 9:
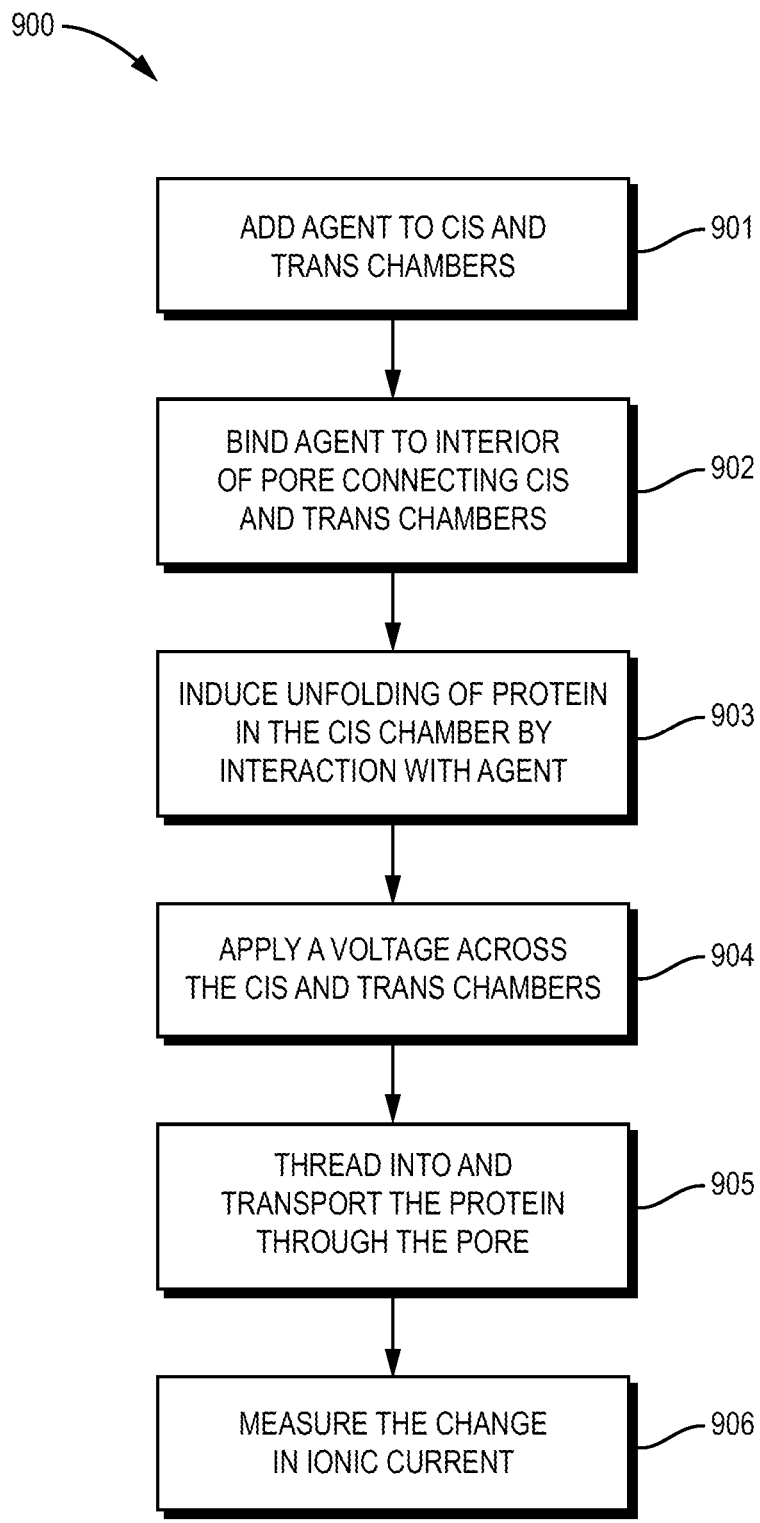
FIG. 9 is a flow chart of a method for transporting a protein through a nanopore and measuring its electronic signature according to a first embodiment of the invention.

FIG. 9 as a flow chart of a method 900 for transporting a protein through a pore and measuring its electronic signature according to a first embodiment of the invention. In step 901, an agent is added to cis and trans chambers separated by a membrane with a pore or nanopore connected the two chambers. The agent may be a chaotrope salt such as guanidinium chloride. The chambers may also include an electrolyte such as KCl. In step 902, the agent, or ions of the agent, bind to the interior of a channel structure defining a pore connecting the trans and cis chambers. These bound agents, are able to induce an electroosmotic flow in the pore that provides a stretching and unfolding force. In step 903, the proteins are unfolded in the cis chamber by interacting with the agent.

In step 904 a voltage is applied across the cis and trans chambers. This voltage induces an ionic current that passes through the pore. In step 905, the protein is threaded into the pore, in some embodiments the treading is assisted with the addition a charged tail to the protein. Also in step 905, the protein is transported through the pore due to the electroosmotic flow generated by the bound agents on the inside of the pore. Finally, in step 906, the change in the ionic current through the pore is measured. The change is created due to the component amino acid residues of the protein blocking ions moving through the pore during its transport. The measured current modulations correspond to the protein's electronic signature and can be used to identify the protein and its component amino acid residues.

Figure 10:
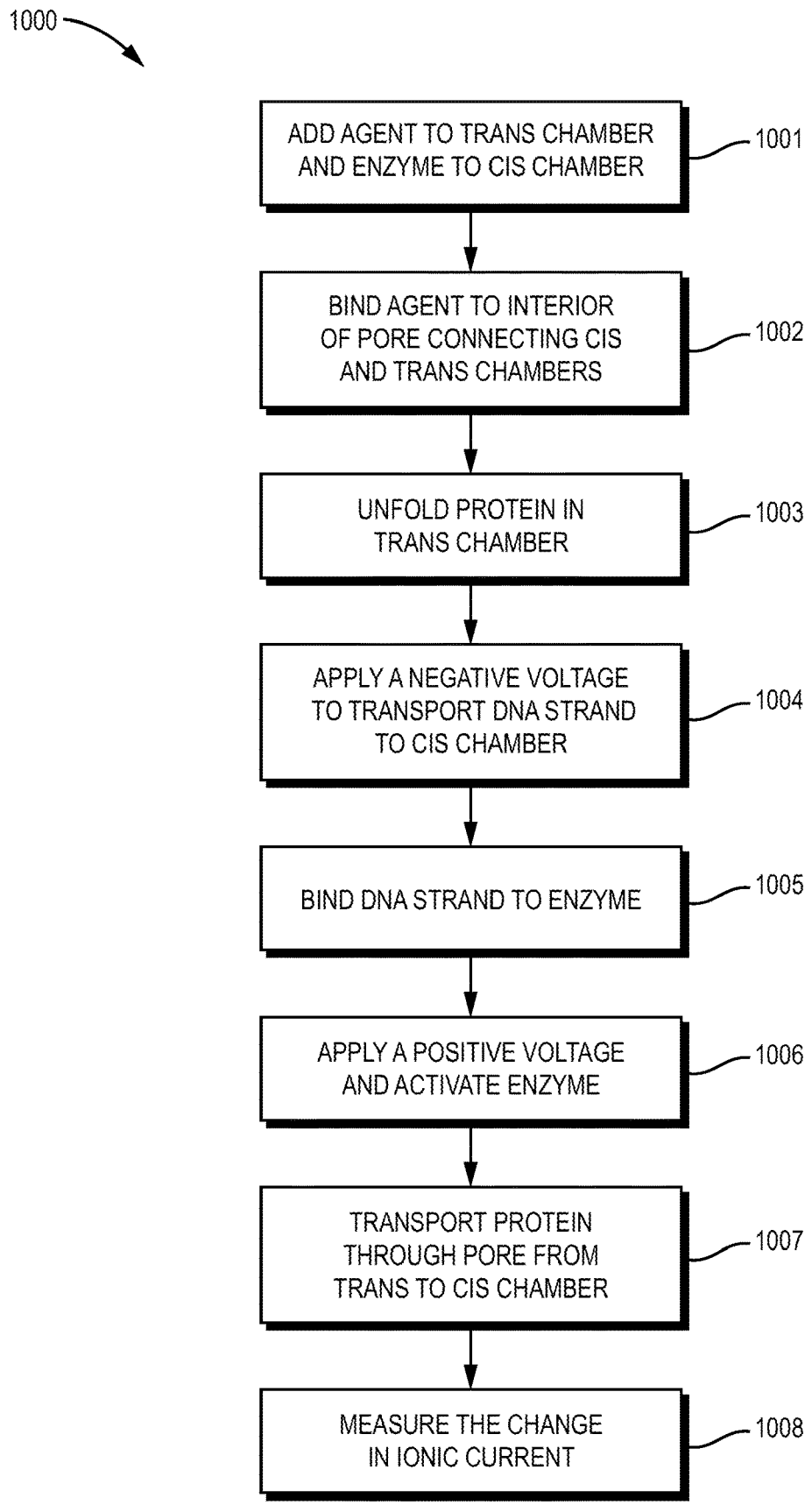
FIG. 10 is a flow chart of a method for transporting a protein through a nanopore and measuring its electronic signature according to a second embodiment of the invention.

FIG. 10 as a flow chart of a method 1000 for transporting a protein through a pore and measuring its electronic signature according to a second embodiment of the invention. In step 1001 an agent is added to the trans chamber and an enzyme is added to a cis chamber. The Cis and trans chambers are separated by a membrane with a pore or nanopore, defined by a channel structure, connected the two chambers. The agent may be a chaotrope reagents such as guanidinium chloride. The chambers may also both include an electrolyte such as KCl. The enzyme is configured to bind a DNA strand and draw, in discrete steps, the bound DNA strand towards the enzyme. In a non-limiting example the enzyme is Hel308. The agent is kept out of the cis chamber to prevent negative interactions with the enzyme. In step 1002, the agent, or ions of the agent, bind to the interior of the channel structure defining the pore connecting the trans and cis chambers. These bound agents, are able to induce an electroosmotic flow in the pore that provides a stretching and unfolding force. In step 1003, the proteins are unfolded in the trans chamber by interacting with the agent. The unfolded proteins include an attached DNA strand. In step 1004, a negative voltage, from the trans chamber to cis chamber, is applied. This negative voltage transports the DNA strand attached to the unfolded protein through the pore and into the cis chamber. In step 1005, the DNA strand binds to the enzyme in the cis chamber.

Next, in step 1006, the voltage is reversed and a positive voltage, from cis chamber to trans chamber, is applied. This positive voltage activates the electroosmotic flow induced by the bound agents in the pore. The electroosmotic flow provides a force towards the trans chamber and a stretching and unfolding force within the pore. Also in step 1006, the enzyme is activated. The activation of the enzyme induces it to pull, in discrete steps the bound DNA strand towards itself and into the cis chamber. This applies a force opposite the force electroosmotic flow. In step 1007, the protein is transported through the pore due to the pulling force applied by the enzyme. However, due to the opposing electroosmotic flow force, the protein remains unfolded and taut during its transport. Finally, in step 1008, the change in the ionic current through the pore is measured. The change is created due to the component amino acid residues of the protein blocking ions moving through the pore during its transport. The measured current modulations correspond to the protein's electronic signature and can be used to identify the protein and its component amino acid residues. Effects of the protein's individual component amino acid residues in the electronic signature should be especially clear and easy to read due to the stretching done by the opposing forces of the pulling force from the enzyme towards the cis chamber and the electroosmotic flow force from the bound agents towards to trans chamber.

FIG. 11A a side-view of a bilayer membrane with a pore supported by a wedge-on-pillar aperture. Planar bilayer membranes 104, 1104 are commonly used to probe isolated trans-membrane channels 105 using a patch-clamp setup. In this setup, two electrodes are used to apply voltage to electrolyte solutions present across a bilayer membrane 104, 1104, for example in chambers 109, 1109 and 110, 1110, which drives ion flow across any available paths through the membrane 104, 1104, for example, a trans-membrane protein channel structure 105, 1105 that define pores or nanopores, such as alpha-hemolysin from *S. aureus*. Typically, the lipid bilayer 104, 1104 is impermeable to ions, which allows sensitive measurements of ion flux across the membrane protein channel structure 105, 1105 that defines a pore or nanopore. A patch-clamp amplifier 108, 1108 may be used to record ion flux through the bilayer 104, 1104 and trans-membrane channel, 105, 1105 for electrolytes containing GdmCl, or other agent 101, 1101. In methods 900 and 1000, this measurement of ion flux provides the electronic signature of the analyzed protein. However, in some conditions the electrolyte contains agents 101, 1101 that compromise the bilayer membrane 104, 1104 stability, which makes single-channel 105, 1105 measurements difficult to conduct. For example, prior art structures and methods have often used Diphytanoyl phosphatidylcholine (DPhPC) to make bilayer membranes 104, 1104 for single-channel 105, 1105 measurements. However, at high concentrations of guanidinium chloride (GdmCl), an agent 101, 1101, that induces protein unfolding, DPhPC membranes 104 are significantly permeable, and previous experiments have typically been limited to low voltage and moderate GdmCl concentrations. In search of a suitable membrane 104 material, amphiphilic block copolymer poly(1,2-butadiene)-b-poly(ethylene oxide) (abbreviated PBD-PEO, cat # P41807C-BdEO, Polymer Source, Montreal, Quebec, Canada) was tested.

FIG. 11B shows the current vs. time trances for BD-PEO bilayers and DPhPC bilayers when voltage increments are applied in opposite polarities in order to test permeability. Element 1112 shows the chemical structure of PBD-PEO and a comparison of a membranes 104, 1104 composed of PBD-PEO 1111 and DPhPC 1113. The chemical structure of $PBD_n$-$PEO_m$ 1112 (n~11, m~8), has an estimated core bilayer 1111 thickness of ~4.4 nm, similar to DPhPC bilayers 1113 (~5.0 nm). The membrane bilayers can be formed by pipette-painting thin organic membrane solutions in decane, a non-limiting example of solution, 103 across a 100 μm diameter wedge-on-pillar aperture. The membranes 104, 1104 are gradually thinned by passing air bubbles across it until a true bilayer is formed, indicated by a rise in membrane capacitance to 70-10 pF, and also by the observation of spontaneous insertion of protein channels 105, 1105 after their addition to the top (cis) chamber 109, 1109.

Graph 1114 is the current vs. time trances for a PBD-PEO bilayer 104, 1104 and graph 1115 is the current vs. time trances for a DPhPC bilayers 104, 1104 with an electrolyte solution of 5 M GdmCl, 1 M KCl, 10 mM Tris, and pH 7.5. These graphs 1114, 1115 show bilayer membrane 104, 1104 ion permeability. The measurements comprising graphs 1114 and 1115 were obtained by applying alternating polarity DC voltages with increasing magnitudes and monitored the leakage current as a function of time using a patch-clamp amplifier 108, 1108. Non-zero current fluctuations correspond to ion leakage through the membranes (indicated by arrows in graphs 1114 and 1115). Traces were low-pass filtered to 10 kHz using the Axopatch internal filter and digitally sampled at 16-bit, 250 kHz using a DAQ card (National Instruments).

FIG. 11C is a graph of the average leakage current vs. voltage for DPhPC and PBD-PEO bilayer membranes for a range of GdmCl concentrations. Lines, with error bars, 1116a-1116f, show the results that illustrate bilayer membrane ion permeability of a DPhPC bilayer membrane 104, 1104 with electrolyte GdmCl concentrations from 0M to 5M. Line, with error bars, 1117 show the result that illustrate bilayer membrane ion permeability of a PBD-PEO bilayer membrane with an electrolyte GdmCl of 5M. The error bars represent standard deviations of the leakage currents. Even in 5 M GdmCl, the PBD-PEO membrane 104, 1104 is impermeable up to 340 mV, whereas significant ion permeability was observed for DPhPC membranes 104, 1104 at lower voltages for all electrolyte conditions.

FIG. 11D is a graph of the critical voltage as a function of GdmCl concentration for DPhPC and PBD-PEO membranes. The critical voltage is defined as the voltage at which the average DC current (Iavg) exceeds 5 pA. Line 1118 is the data for a PBD-PEO membrane 104, 1104. Line 1119 is the data for a DPhPC membrane 104, 1104. The rapid decline in voltage stability for DPhPC suggests a significant membrane destabilization, possibly through formation of interactions with phosphate groups of DPhPC. In contrast, PBD-PEO has an outstanding chemical resilience to GdmCl concentrations that are high enough to denature most proteins. This resilience allows the use of agents that include GdmCl to be used in methods 900 and 1000 to induce protein unfolding and/or provide the essential intra pore forces.

Figure 12A:
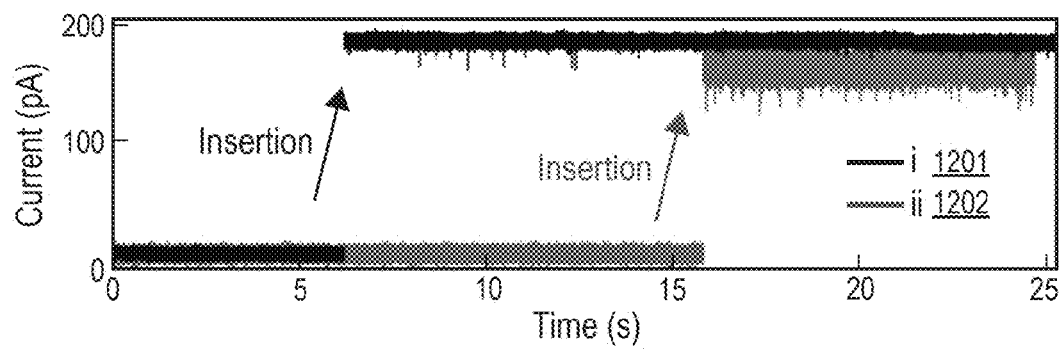
FIG. 12A shows the current trances before and immediately following single-channel insertion into PBD-PEO bilayer membranes.

FIG. 12A shows the current trances before and immediately following single-channel insertion into PBD-PEO bilayer membranes. FIG. 12A shows the current traces for alpha-hemolysin 1202 from *S. aureus* (Sigma-Aldrich, Cat # H9395) and an engineered MspA channel 1201 from *M. smegmatis*, M2-Msp. The electrolyte mixture used was 1 M KCl, 1.5 M GdmCl, 10 mM Tris, pH 7.5 and it was subjected to V=100 mV. As seen in the traces 1201 and 1202, both M2-MspA and α-hemolysin channel structure 105 defining a pore or nanopore in a PBD-PEO bilayer membrane 104 produce stable current levels, as routinely observed with DPhPC membranes. This illustrates, that pore conductivity is not negatively affected when using the more stable PBD-PEO bilayer membrane 104.

Figure 12B:
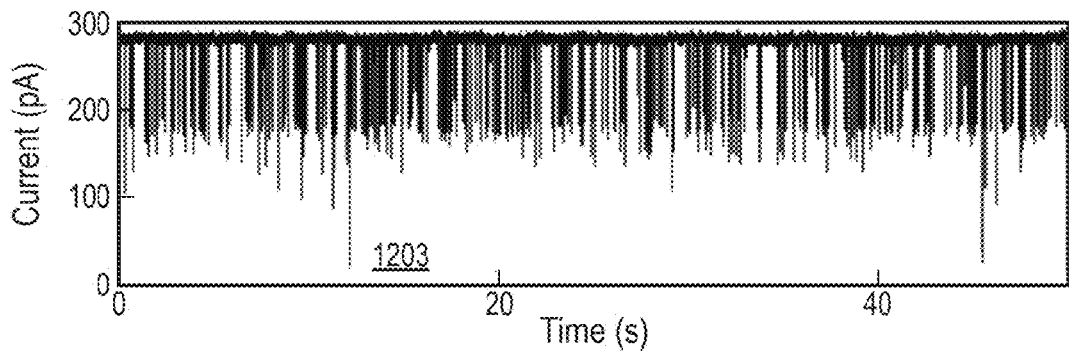
FIG. 12B is a 2.5 second recording at 150 mV of an M2-MspA channel with spikes caused by the addition of a short (15-nt) single-stranded DNA to the cis chamber.

FIG. 12B is a 2.5 second recording at 150 mV of an M2-MspA channel with spikes caused by the addition of a short (15-nt) single-stranded DNA to the cis chamber. The channel 105 shows normal activity and a high rate of events 1203, current fluctuations, caused by DNA interactions with the M2-MspA channel 105. The added DNA was 1.8 μM 15-nt single-stranded DNA and was originally placed in cis chamber 109. The electrolyte mixture was 1 M KCl, 10 mM Tris, pH 7.5 and a voltage of V=150 mV was applied by voltage source 108.

Figure 12C:
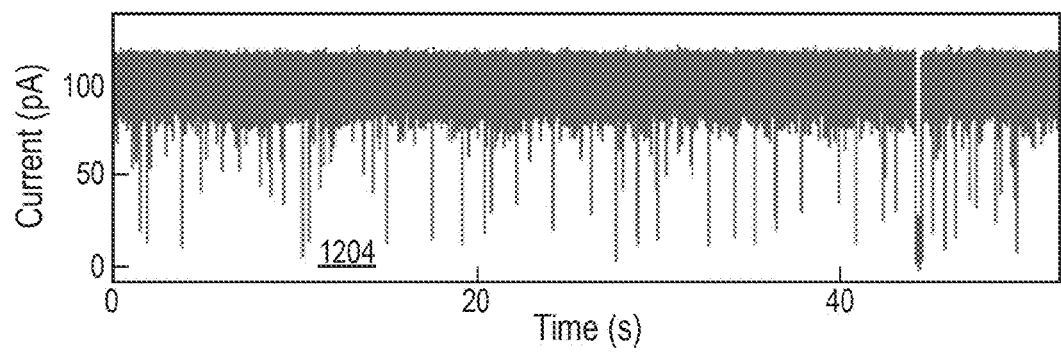
FIG. 12C is a 52 second recording at 150 mV of an alpha-hemolysin channel with spikes caused by the addition of a 60-nt single-stranded DNA to the cis chamber.

FIG. 12C is a 52 second recording at 150 mV of an alpha-hemolysin channel with spikes caused by the addition of a 60-nt single-stranded DNA to the cis chamber. The channel 105 shows normal activity and a high rate of events 1204, current fluctuations, caused by DNA interactions with the alpha-hemolysin channel 105. The added DNA was 1 μM 60-nt single-stranded DNA. The electrolyte mixture was 1 M KCl, 10 mM Tris, pH 7.5 and a voltage of V=150 mV was applied by voltage source 108. In both FIGS. 12 B and 12C, traces were low-pass filtered to 10 kHz using the Axopatch internal filter and digitally sampled at 16-bit, 250 kHz using a DAQ card. As with the M2-MspA data in FIG. 12B, the alpha-hemolysin channel 105 is fully active, as evidenced by the stable baseline current and a "healthy" rate of events. Based on these data, the suitability of PBD-PEO bilayer membranes 104 for single-channel 105 recordings is confirmed. Therefore, PBD-PEO bilayer membranes 104 and M2-MspA can be used in both methods 900 and 1000 in addition to high concentrations of chaotropic agents 101 such as guanidinium chloride.

Figure 12D:
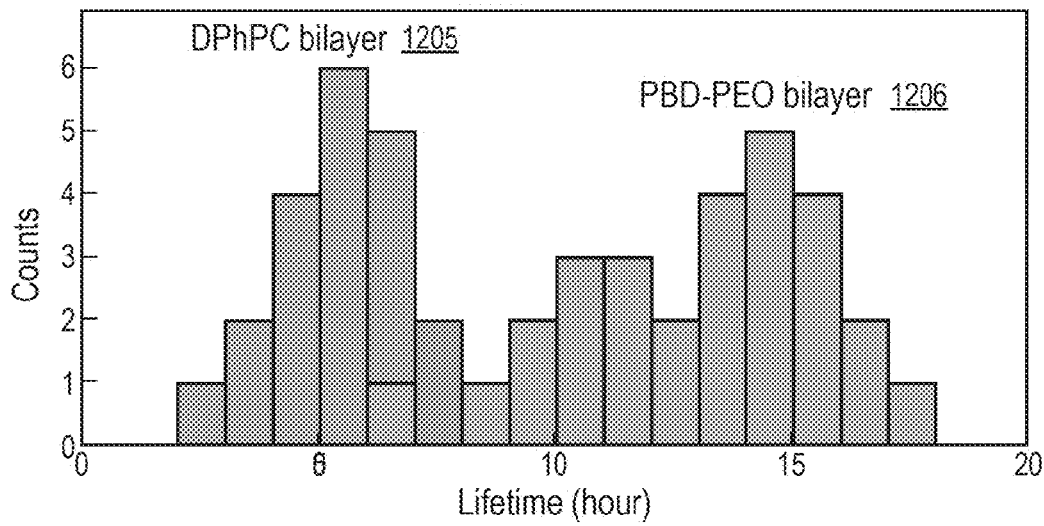
FIG. 12D shows the histograms of bilayer membrane lifetimes, measured by monitoring the current as a function of time for a sealed fluidic cell and recording the time it takes for the bilayers to rupture in 1M KCl, 10 mM Tris, pH 7.5 electrolyte.

FIG. 12D shows the histograms of bilayer membrane lifetimes, measured by monitoring the current as a function of time for a sealed fluidic cell and recording the time it takes for the bilayers to rupture in 1M KCl, 10 mM Tris, pH 7.5 electrolyte. Histogram 1205 is the data (n=20) for a DPhPC bilayer membrane 104 and histogram 1206 is the data (n–30) for a PBD-PEO bilayer membrane 104. The lifetime distribution for PBD-PEO bilayers shows a 2-fold to 3-fold increase in membrane survival lifetime as compared to DPhPC membranes. In addition, PBD-PEO polymers were used that had been stored in chloroform at 4° C. for up to 17 months and no performance degradation was observed. In contrast, DPhPC lipids typically degrade within months if not stored with care at −20° C. under conditions that minimize oxidation/hydrolysis.

The proven stable PBD-PEO bilayer membranes 104 were used to test the structural integrity of the α-hemolysin channel structure 105 defining a pore or nanopore at high GdmCl, acting as agent 101, concentrations. It was thought that urea concentrations might denature the α-hemolysin vestibule cap. To test this possibility, a DNA-based molecular probe was used to test the vestibule cap intactness. Short, blunt DNA hairpins are known to produce distinct signatures in α-hemolysin through long-lived interactions with their vestibule regions. These interactions are so intricate that DNA hairpins of different stem lengths can be distinguished with 1 bp resolution.

Figures 13A, 13B, 13C, 13D:
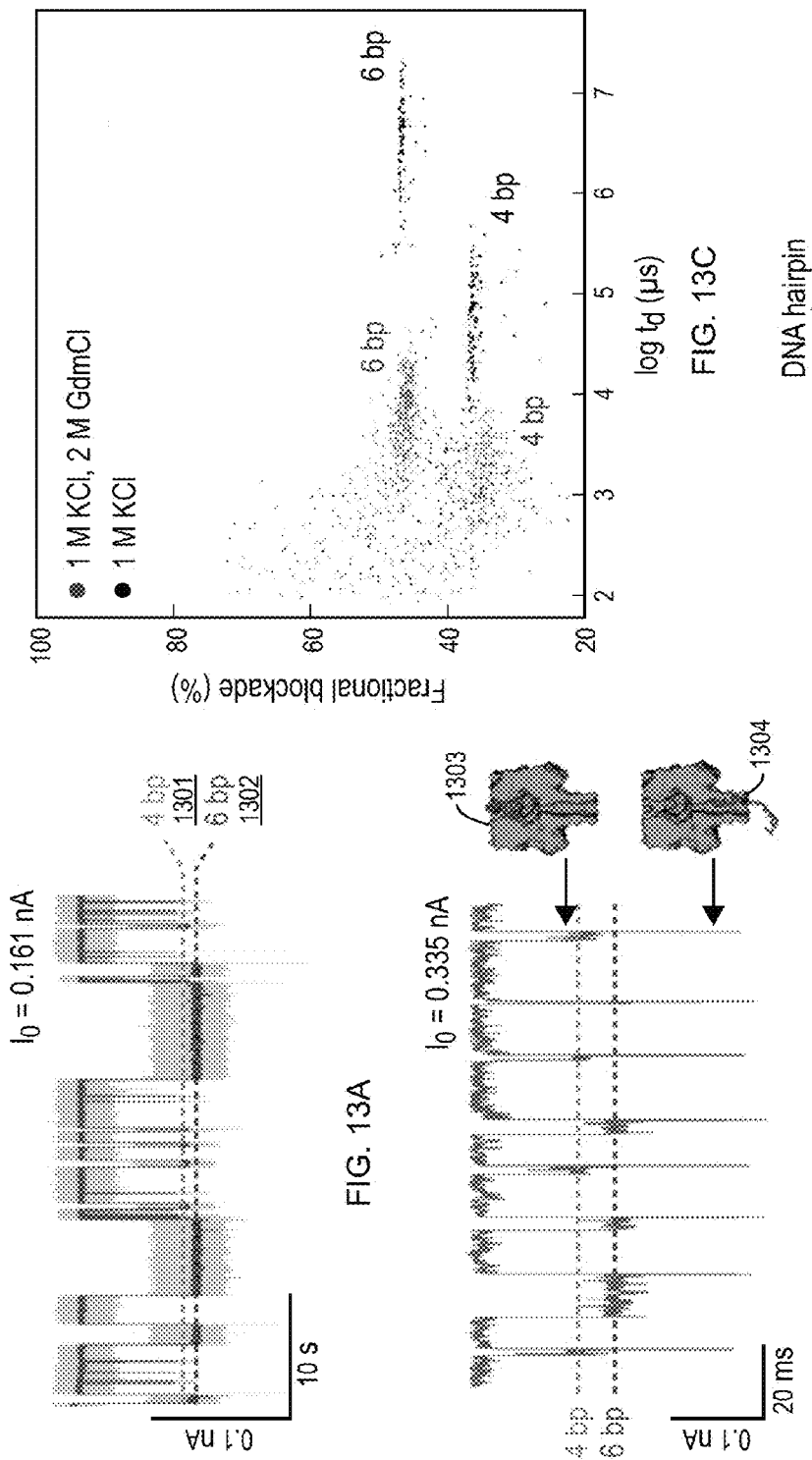
FIG. 13A shows current vs. time trace obtained for an α-hemolysin channel when a mixture of 4 bp (0.4 µM) and 6 bp (0.6 µM) blunt DNA hairpins with a T4 loop is added to the cis chamber with an electrolyte mixture that included 1M KCl.
FIG. 13B shows current vs. time trace obtained for an α-hemolysin channel when a mixture of 4 bp (0.4 µM) and 6 bp (0.6 µM) blunt DNA hairpins with a T4 loop is added to the cis chamber with an electrolyte mixture that included 1M KCl and 2 M GdmCl.
FIG. 13C shows a scatter plot of fractional blockades vs. event dwell times for the two experiments from FIGS. 12A and 12B.
FIG. 13D shows a DNA hairpin interacting with an α-hemolysin channel structure.

FIG. 13D shows a DNA hairpin interacting with an α-hemolysin channel structure defining a pore. The DNA hairpin may be a mixture of 4 bp and 6 bp blunt hairpins with sequences 5'-CTCGTTTTCGAG-3' and 5'-CTAACGTTTTCGTTAG-3', respectively added to cis chamber 109.

FIG. 13A shows current vs. time trace obtained for an α-hemolysin channel when a mixture of 4 bp (0.4 μM) and 6 bp (0.6 μM) blunt DNA hairpins with a T4 loop is added to the cis chamber with an electrolyte mixture that included 1M KCl. The electrolyte mixture also contained 10 mM Tris, pH 7.5 and the voltage applied was V=175 mV. Long-lived events, current fluctuations, with two characteristic amplitude levels, 1301 and 1302, were obtained, which correspond to the expected levels for the added DNA hairpin lengths 4 bp and 6 bp respectively.

FIG. 13B shows current vs. time trace obtained for an α-hemolysin channel when a mixture of 4 bp (0.4 μM) and 6 bp (0.6 μM) blunt DNA hairpins with a T4 loop is added to the cis chamber with an electrolyte mixture that included 1M KCl and 2 M GdmCl. The electrolyte mixture also contained 10 mM Tris, pH 7.5 and the voltage applied was V=175 mV. The addition of 2 M GdmCl produces much faster events, current variations, that exclusively contain two levels, an intermediate blockade level with relatively long (~ms) timescale 1303, followed by a rapid deep level 1304, which can be attribute to translocation of the denatured DNA hairpin. Representations of the DNA hairpin's interaction with the α-hemolysin are provided for both event 1303 and 1304.

FIG. 13C shows a scatter plot of fractional blockades vs. event dwell times for the two experiments from FIGS. 12A and 12B. The scatter plots reveal dwell times that are on average 2-3 orders of magnitude shorter than for 1 M KCl buffer alone, although the fractional blockade levels for the observed events are very similar (<2% difference) for both electrolyte conditions.

The teachings of all patents, published applications and references cited herein are incorporated by reference in their entirety. The effect of urea on disrupting DNA and RNA secondary structures is known and have been reported to facilitate transport of structured nucleic acids through α-hemolysin channels. Similarly, it is shown by the data in FIG. 13C that 2 M GdmCl disrupts secondary structure in short DNA hairpins, while not resulting in measurable structural changes to the α-hemolysin vestibule cap. Therefore α-hemolysin channel structure defining 105 pores or nanopores are also viable for use in methods 900 and 1000 in addition to high concentrations of chaotropic agents 101 such as guanidinium chloride. Other examples of chaotropic agents useful in the methods and systems described herein include n-butanol, ethanol, lithium perchlorate, lithium acetate, magnesium chloride, phenol, 2-propanol, sodium dodecyl sulfate, thiourea, and urea In summary, it has been demonstrated that that bilayer membranes 104 composed of PBD-PEO amphiphilic diblock copolymer are suitable for single-channel 105 recordings in presence of high GdmCl 101 concentrations. Membrane lifetimes are superior to prior art DPhPC lipid membranes, and reconstitution of protein channels readily occurs. It has also been demonstrated that t the vestibule cap of α-hemolysin channel structure 105 maintains its integrity at 2 M GdmCl concentrations, while significantly destabilizing the secondary duplex structures of short blunt DNA hairpins.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method of performing single molecule proteomics, the method comprising:
    containing a fluid in a structure, the structure defining an interior cavity and a barrier dividing the interior cavity into a first chamber and a second chamber, the barrier containing a channel structure defining a nanopore therethrough fluidically coupling the first and second chambers, the nanopore having a flow path bounded by an interior surface of the channel structure; wherein the fluid includes (i) a protein comprising amino acid residues and, (ii) an agent, the agent capable of enabling stretching and unfolding of the protein;
    binding particles of the agent to the interior surface of the channel structure defining the nanopore to establish bound particles, the bound particles causing the amino acid residues of the protein passing through the flow path of the nanopore to orient themselves as a linear series of amino acid residues;
    applying a voltage gradient between the first chamber and the second chamber via the flow path, the voltage gradient inducing an ionic flow through the flow path of the nanopore;
    observing an electronic signature produced by interactions between ions comprising the ionic flow and the linear series of amino acid residues of the protein passing through the flow path of the nanopore altering the ionic current through the flow path of the nanopore; and
    determining a property of the protein based on the observed electronic signature.

2. The method of claim 1 wherein the agent includes guanidinium ions.

3. The method of claim 1 wherein binding the particles of the agent includes the bound particles causing the amino acid residues of the protein passing through the flow path of the nanopore to orient themselves as a linear series of amino acid residues by generating an electroosmotic force in the flow path of the nanopore.

4. The method of claim 3 wherein the electroosmotic force varies linearly with respect to a magnitude of the voltage gradient.

5. The method of claim 1 further comprising connecting the protein to a charged tail configured to guide the protein into the flow path when the voltage gradient is applied.

6. The method of claim 1 further comprising containing in the first chamber an enzyme that is capable of causing the protein to unfold.

7. The method of claim 6 wherein the agent is not present in the first chamber.

8. The method of claim 1 wherein the voltage gradient is a first voltage gradient, and wherein the method further comprises:
    connecting a DNA tail to the protein;
    applying a second voltage gradient across the first and the second chambers via the flow path, the second voltage gradient of sufficient strength to cause a section of the DNA tail to pass through the nanopore prior to applying the first voltage gradient; and
    activating an enzyme, contained in the first chamber, to draw, in discrete steps, the DNA tail and the connected protein toward the enzyme through the flow path.

9. The method of claim 8 wherein a DNA structure is attached to the nanopore, the DNA structure configured to maintain separation between the enzyme and the nanopore.

10. The method of claim 1 wherein the property of the protein is at least one of: an identity of the protein and an amino acid residue sequence of the protein.

11. A system for performing single molecule proteomics, the system comprising:
    a structure defining an interior cavity and a barrier dividing the interior cavity into a first chamber and a second chamber, the barrier containing a channel structure defining a nanopore therethrough fluidically coupling the first and second chambers, the nanopore having a flow path bounded by an interior surface of the channel structure, wherein the fluid includes (i) a protein comprising amino acid residues and, (ii) an agent, the agent, wherein particles of the agent are bound the interior surface of the channel structure defining the nanopore, the bound particles cause the amino acid residues of the protein that pass through the flow path of the nanopore to orient themselves as a linear series of amino acid residues;

a voltage source configured to apply a voltage gradient between the first and second chambers via the flow path, the voltage gradient inducing an ionic flow through the flow path of the nanopore;

a detector configured to observe an electronic signature produced by interactions between ions comprising the ionic flow and the linear series of amino acid residues of the protein passing through the flow path of the nanopore altering the ionic current through the flow path of the nanopore; and a processor configured to determine a property of the protein based on the electronic signature.

12. The system of claim 11 wherein the agent includes guanidinium ions.

13. The system of claim 11 wherein the channel structure is at least one of a membrane protein and a solid-state nanopore.

14. The system of claim 11 wherein the protein is connected to a charged tail configured to guide the protein into the flow path when the voltage gradient is applied.

15. The system of claim 11 wherein the first chamber includes an enzyme that unfolds the protein.

16. The system of claim 15 wherein the enzyme that unfolds the protein is unfoldase.

17. The system of claim 11, wherein the voltage gradient is a first voltage gradient, and wherein:

the protein is connected to a DNA tail;

the voltage source is further configured to apply a second voltage gradient between the first and the second chambers via the flow path, the second voltage gradient of sufficient strength to cause a section of the DNA tail to pass through the nanopore prior to the voltage source applying the first voltage gradient; and the first chamber of the structure contains an enzyme, capable of drawing, in discrete steps, the DNA tail and the connected protein toward the enzyme through the flow path.

18. The system of claim 17 wherein the DNA tail comprises of a front portion of single-stranded DNA, a middle portion of double-stranded DNA, and a back portion of single-stranded DNA, wherein the front portion of single-strand DNA is the section of the DNA tail passed through the nanopore prior to the voltage source applying the first voltage gradient.

19. The system of claim 17 further comprising a DNA structure attached to the nanopore, the DNA structure configured to maintain separation between the enzyme and the nanopore.

20. The system of claim 11 wherein the property of the protein is at least one of an identity of the protein and an amino acid residue sequence of the protein.

* * * * *

UNITED STATES PATENT AND TRADEMARK OFFICE
CERTIFICATE OF CORRECTION

PATENT NO. : 11,994,508 B2  
APPLICATION NO. : 17/645943  
DATED : May 28, 2024  
INVENTOR(S) : Meni Wanunu et al.

Page 1 of 1

It is certified that error appears in the above-identified patent and that said Letters Patent is hereby corrected as shown below:

In the Claims

In Claim 11, Column 21, Lines 1 to 2:
Delete "an agent, the agent, wherein" and insert -- an agent, the agent capable of enabling stretching and unfolding of the protein, wherein --.

Signed and Sealed this  
Thirty-first Day of December, 2024

Derrick Brent  
*Acting Director of the United States Patent and Trademark Office*